United States Patent [19]
Leung et al.

[11] Patent Number: 5,952,480
[45] Date of Patent: Sep. 14, 1999

[54] MAMMALIAN CDP-DIACYLGLYCEROL SYNTHASE

[75] Inventors: David W. Leung, Mercer Island; Reitha Weeks, Seattle, both of Wash.

[73] Assignee: Cell Therapeutics, Inc., Seattle, Wash.

[21] Appl. No.: 08/672,814

[22] Filed: Jun. 28, 1996

[51] Int. Cl.$^6$ .................................................... C12N 15/54
[52] U.S. Cl. ............................................ 536/23.2; 435/194
[58] Field of Search ............................. 536/23.2; 435/144

[56] References Cited

PUBLICATIONS

Hancock, A. M., et. al. (1996) J. Neurochem. 67(5), 2200–2203.

Saito, S., et. al. (1997) J. Biol. Chem. 272(14), 9503–9509.

Icho, T., et. al. (1985) J. Biol. Chem. 260(22), 12078–12083.

*Primary Examiner*—Charles L. Patterson, Jr.
*Attorney, Agent, or Firm*—Susan J. Friedman; Stephen Faciszewski

[57] ABSTRACT

There is disclosed cDNA sequences and polypeptides having the enzyme CDP-diacylglycerol synthase (CDS) activity. CDS is also known as CTP:phosphatidate cytidylytransferase. There is further disclosed methods for isolation and production of polypeptides involved in phosphatidic acid metabolism and signaling in mammalian cells, in particular, the production of purified forms of CDS.

1 Claim, 18 Drawing Sheets

FIG. 1

```
          10         20         30         40         50         60
TCTATGGTGG GGCCGCGTTA GTGGCTGCGG CTCCGGGGA CTCCAGGGCG CGGCTGCGAG
          70         80         90        100        110        120
GTGGCGGGGC GCCCCGCCTG CAGAACCCTG CTTGCAGCTC AGGTTTCGGG GTGCTTGAGG
         130        140        150        160        170        180
AGGCCGCCAC GGCAGCGCGG GAGCGGAAGA TGTTGGAGCT GAGGCACCGG GGAAGCTGCC
         190        200        210        220        230        240
CCGGCCCCAG GGAAGCGGTG TCGCCGCCAC ACCCGCGAGGG AGAGGCGGCC GGCGGCGACC
         250        260        270        280        290        300
ACGAAACCGA GAGCACCAGC GACAAAGAAA CAGATATTGA TGACAGATAT GGAGATTGG
         310        320        330        340        350        360
ATTCCAGAAC AGATTCTGAT ATTCCGGAAA TTCCACCATC CTCAGATAGA ACCCCTGAGA
         370        380        390        400        410        420
TTCTCAAAAA AGCTCTATCT GGTTTATCTT CAAGGTGGAA AAACTGGTGG ATACGTGGAA
         430        440        450        460        470        480
TTCTCACTCT AACTATGATC TCGTTGTTTT TCCTGATCAT CTATATGGGA TCCTTCATGC
         490        500        510        520        530        540
TGATGCTTCT TGTTCTGGGC ATCCAAGTGA AATGCTTCCA TGAAATTATC ACTATAGTT
         550        560        570        580        590        600
ATAGAGTCTA TCATTCTTAT GATCTACCAT GGTTTAGAAC ACTAAGTTGG TACTTTCTAT
```

FIG. 1 (cont'd)

```
         610        620        630        640        650        660
  TGTGTGTAAA CTACTTTTTC TATGGAGAGA CTGTAGCTGA TTATTTTGCT ACATTGTTC 670        680        690        700        710        720
  AAAGAGAAGA ACAACTTCAG TTCCTCATTC GCTACCATAG ATTTATATCA TTTGCCCTCT 730        740        750        760        770        780
  ATCTGGCAGG TTTCTGCATG TTTGTACTGA GTTTGGTGAA GGAACATTAT CGTCTGCAGT 790        800        810        820        830        840
  TTTATATGTT CGCATGGACT CATGTCACTT TACTGATAAC TGTCACTCAG TCACACCTTG 850        860        870        880        890        900
  TCATCCAAAA TCTGTTTGAA GGCATGATAT GGTTCCTTGT TCCAATATCA AGTGTTATCT 910        920        930        940        950        960
  GCAATGACAT AACTGCTTAC CTTTTTTGGAT TTTTTTTTGG GAGAACTCCA TTAATTAAGT 970        980        990       1000       1010       1020
  TGTCTCCTAA AAAGACTTGG GAAGGATTCA TTGGTGGTTT CTTTTCCACA GTTGTGTTTG 1030       1040       1050       1060       1070       1080
  GATTCATTGC TGCCTATGTG TTATCCAAAT ACCAGTACTT TGTCTGCCCA GTGGAATACC 1090       1100       1110       1120       1130       1140
  GAAGTGATGT AAACTCCTTC GTGACAGAAT GTGAGCCCTC AGAACTTTTC CAGCTTCAGA
```

FIG. 1 (cont'd)

```
     1150       1160       1170       1180       1190       1200
CTTACTCACT TCCACCCTTT CTAAAGGCAG TCTTGAGACA GGAAAGAGTG AGCTTGTACC 1210       1220       1230       1240       1250       1260
CTTTCCAGAT CCACAGCATT GCACTGTCAA CCTTTGCATC TTTAATTGGC CCATTTGGAG 1270       1280       1290       1300       1310       1320
GCTTCTTTGC TAGTGGATTC AAAAGAGCCT TCAAAAATCAA GGATTTTGCA AATACCATTC 1330       1340       1350       1360       1370       1380
CTGGACATGG TGGGATAAATG GACAGATTTG ATTGTCAGTA TTTGATGGCA ACTTTGGTAC 1390       1400       1410       1420       1430       1440
ATGGNTACAT CACAAGTTTT ATAAGGGGCC CAAATCCCAG CAAAGTGCTA CAGCAGTTGT 1450       1460       1470       1480       1490       1500
TGGTGCTTCA ACCTGAACAG CAGTTAAATA TATATAAAAC CCTGAAGACT CATCTCATTG 1510       1520       1530       1540       1550       1560
AGAAAGGAAT CCTACAACCC ACCTTGAAGG TATAACTGGA AAACACTGAC TCCAGAGAGG GAAGGACTGA 1570       1580       1590       1600       1610       1620
CAAGAAGGAA TTATTCAGAA AAACACTGAC AGATGTTTTA TAAATTGTAC AGAAAAATAG 1630       1640       1650       1660       1670       1680
TTAAAAATGC AATAGGTTGA AGTTTTGGAG ATATGTTTCT CTCTGAAATT ACTGTGAATA
```

FIG. 1 (cont'd)

```
        1690        1700        1710        1720        1730        1740
TTTAACAAAC  ACTTACTTGA  TCTATGTTAT  GAAATAAGTA  GCAAATTGCC  AGCAAAATGT 1750        1760        1770        1780        1790        1800
CTTGTACCTT  TTCTAAAGTG  TATTTTCTGA  TGTGAACTTC  CTTCCCCTTA  CTTGCTAGGT 1810        1820        1830        1840        1850        1860
TTCATAATTT  AAAAGACTGG  TATTTAAAAG  AGTCAAACAC  TATAAAATGA  GTAAGTTGAC 1870        1880        1890        1900        1910        1920
GATGTTTTAA  GATTGCACCT  GGCAGTGTGC  CTTTTTGCAC  AAATATTTAC  TTTTGCACTT 1930        1940        1950        1960        1970        1980
GGAGCTGCTT  TTAATTTTAG  CAAAAATGTTT  TATGCAAGGC  ACAATAGGAA  GTCAGTTCTC 1990        2000        2010        2020        2030        2040
CTGCACTTCC  TCCTCATGTA  GTCTGGAGTA  CTTTCTAAAG  GGCTTAGTTG  GATTTAAAAA 2050        2060        2070        2080        2090        2100
AAAAAAAAAA  AGGGGCGGCCG  CTCTAGAGGA  TCCCTCGAGG  GGCCCAAGCT  TACGCGTGCA 2110        2120        2130        2140        2150        2160
TGC......    ......     ......     ......     ......     ......
```

FIG. 2

```
  1  TCTATGGTGGGGCCGCGTTAGTGGCTGCCGCTCCGCGGACTCCAGGGCGCGGCTGCGAGGT   62
 63  GGCGGGGGCCCCGCCTGCAGAACCCTGCTTGCAGCTTCAGGTTTCGGGGTGCTTGAGGAG  122

123  GCCGCCACGGCGGGAGCGGGGAAG ATG TTG GAG CTG AGG CAC CGG GGA       173
  1                           Met Leu Glu Leu Arg His Arg Gly        8

174  AGC TGC CCC GGC GAA GCG GTG TCG CCG CCA CAC CGC GAG            218
  9  Ser Cys Pro Gly Arg Glu Ala Val Ser Pro Pro His Arg Glu         23

219  GGA GAG GCG GCC GGC GAC CAC GAA ACC GAG AGC ACC AGC GAC        263
 24  Gly Glu Ala Ala Gly Asp His Glu Thr Glu Ser Thr Ser Asp         38

264  AAA GAA ACA GAT ATT GAT GAC AGA TAT GGA GAT TTG GAT TCC AGA    308
 39  Lys Glu Thr Asp Ile Asp Asp Arg Tyr Gly Asp Leu Asp Ser Arg     53

309  ACA GAT TCT GAT ATT CCG GAA ATT CCA CCA TCC TCA GAT AGA ACC    353
 54  Thr Asp Ser Asp Ile Pro Glu Ile Pro Pro Ser Ser Asp Arg Thr     68

354  CCT GAG ATT CTC AAA AAA GCT CTA TCT GGT TTA TCT TCA AGG TGG    398
 69  Pro Glu Ile Leu Lys Lys Ala Leu Ser Gly Leu Ser Ser Arg Trp     83

399  AAA AAC TGG TGG ATA CGT GGA ATT CTC ACT CTA ACT ATG ATC TCG    443
 84  Lys Asn Trp Trp Ile Arg Gly Ile Leu Thr Leu Thr Met Ile Ser     98
```

FIG. 2 (cont'd)

```
444  TTG TTT TTC CTG ATC TAT ATG GGA TCC TTC ATG CTG ATG CTT  488
 98  Leu Phe Phe Leu Ile Tyr Met Gly Ser Phe Met Leu Met Leu  113

489  CTT GTT CTG GGC ATC CAA GTG AAA TGC TTC CAT GAA ATT ATC ACT  533
113  Leu Val Leu Gly Ile Gln Val Lys Cys Phe His Glu Ile Ile Thr  128

534  ATA GGT TAT AGA GTC TAT CAT TCT TAT GAT CTA CCA TGG TTT AGA  578
128  Ile Gly Tyr Arg Val Tyr His Ser Tyr Asp Leu Pro Trp Phe Arg  143

579  ACA CTA AGT TGG TAC TTT CTA TTG TGT GTA AAC TAC TTT TTC TAT  623
143  Thr Leu Ser Trp Tyr Phe Leu Leu Cys Val Asn Tyr Phe Phe Tyr  158

624  GGA GAG ACT GTA GCT GAT TAT TTT GCT ACA TTT GTT CAA AGA GAA  668
158  Gly Glu Thr Val Ala Asp Tyr Phe Ala Thr Phe Val Gln Arg Glu  173

669  GAA CAA CTT CAG TTC CTC ATT CGC TAC CAT AGA TTT ATA TCA TTT  713
173  Glu Gln Leu Gln Phe Leu Ile Arg Tyr His Arg Phe Ile Ser Phe  188

714  GCC CTC TAT CTG GCA GGT TTC TGC ATG TTT GTA CTG AGT TTG GTG  758
188  Ala Leu Tyr Leu Ala Gly Phe Cys Met Phe Val Leu Ser Leu Val  203

759  AAG GAA CAT TAT CGT CTG CAG TTT TAT ATG TTC GCA TGG ACT CAT  803
203  Lys Glu His Tyr Arg Leu Gln Phe Tyr Met Phe Ala Trp Thr His  218
```

FIG. 2 (cont'd)

```
 804 GTC ACT TTA CTG ATA ACT GTC ACT CAG TCA CAC CTT GTC ATC CAA  848
 218 Val Thr Leu Leu Ile Thr Val Thr Gln Ser His Leu Val Ile Gln  233

849 AAT CTG TTT GAA GGC ATG ATA TGG TTC CTT GTT CCA ATA TCA AGT  893
 233 Asn Leu Phe Glu Gly Met Ile Trp Phe Leu Val Pro Ile Ser Ser  248

894 GTT ATC TGC AAT GAC ATA ACT GCT TAC CTT TTT GGA TTT TTT TTT  938
 248 Val Ile Cys Asn Asp Ile Thr Ala Tyr Leu Phe Gly Phe Phe Phe  263

939 GGG AGA ACT CCA TTA ATT AAG TTG TCT CCT AAA ACT TGG GAA       983
 263 Gly Arg Thr Pro Leu Ile Lys Leu Ser Pro Lys Thr Trp Glu       278

984 GGA TTC ATT GGT GGT GGG TTC TTT TCC ACA GTT GTG TTT GGA TTC ATT 1028
 278 Gly Phe Ile Gly Gly Gly Phe Phe Ser Thr Val Val Phe Gly Phe Ile 293

1029 GCT GCC TAT GTG TTA TCC AAA TAC CAG TAC TTT GTC TGC CCA GTG 1073
 293 Ala Ala Tyr Val Leu Ser Lys Tyr Gln Tyr Phe Val Cys Pro Val  308

1074 GAA TAC CGA AGT GAT GTA AAC TCC TTC GTG ACA GAA TGT GAG CCC 1118
 308 Glu Tyr Arg Ser Asp Val Asn Ser Phe Val Thr Glu Cys Glu Pro  323

1119 TCA GAA CTT TTC CAG CTT TAC TCA ACT TAC TCA CTT CCA CCC TTT CTA 1163
 323 Ser Glu Leu Phe Gln Leu Gln Thr Tyr Ser Leu Pro Pro Phe Leu  338
```

FIG. 2 (cont'd)

| | | | | | | | | | | |
|---|---|---|---|---|---|---|---|---|---|---|
| 1164 | AAG | GCA | GTC | TTG | AGA | CAG | GAA | AGA | GTG | AGC | TTG | TAC | CCT | TTC | CAG | 1208 |
| 338 | Lys | Ala | Val | Leu | Arg | Gln | Glu | Arg | Val | Ser | Leu | Tyr | Pro | Phe | Gln | 353 |
| 1209 | ATC | CAC | AGC | ATT | GCA | CTG | TCA | ACC | TTT | GCA | TCT | ATT | GGC | CCA | 1253 |
| 353 | Ile | His | Ser | Ile | Ala | Leu | Ser | Thr | Phe | Ala | Ser | Leu | Ile | Gly | Pro | 368 |
| 1254 | TTT | GGA | GGC | TTC | TTT | GCT | AGT | GGA | TTC | AAA | AGA | GCC | TTA | ATT | 1298 |
| 368 | Phe | Gly | Gly | Phe | Phe | Ala | Ser | Gly | Phe | Lys | Arg | Ala | Leu | Ile | Ile | 383 |
| 1299 | AAG | GAT | TTT | GCA | AAT | ACC | ATT | CCT | GGA | CAT | GGT | GGG | ATA | ATG | GAC | 1343 |
| 383 | Lys | Asp | Phe | Ala | Asn | Thr | Ile | Pro | Gly | His | Gly | Gly | Ile | Met | Asp | 398 |
| 1344 | AGA | TTT | GAT | TGT | CAG | TAT | TTG | ATG | GCA | ACT | TTG | GTA | CAT | GGN | TAC | 1388 |
| 398 | Arg | Phe | Asp | Cys | Gln | Tyr | Leu | Met | Ala | Thr | Leu | Val | His | Gly | Tyr | 413 |
| 1389 | ATC | ACA | AGT | TTT | ATA | AGG | GGC | CCA | AAT | CCC | AGC | AAA | GTG | CTA | CAG | 1433 |
| 413 | Ile | Thr | Ser | Phe | Ile | Arg | Gly | Pro | Asn | Pro | Ser | Lys | Val | Leu | Gln | 428 |
| 1434 | CAG | TTG | GTG | CTT | ATA | CAA | CAG | CAG | GAA | CAG | CAG | TTA | AAT | ATA | TAT | AAA | 478 |
| 428 | Gln | Leu | Val | Leu | Ile | Gln | Gln | Gln | Glu | Gln | Gln | Leu | Asn | Ile | Tyr | Lys | 43 |
| 1479 | ACC | CTG | AAG | ACT | CAT | CTC | ATT | GAG | AAA | GGA | ATC | CTA | CAA | CCC | ACC | 523 |
| 443 | Thr | Leu | Lys | Thr | His | Leu | Ile | Glu | Lys | Gly | Ile | Leu | Gln | Pro | Thr | 458 |

FIG. 2 (cont'd)

```
1524  TTG AAG GTA TAA CTGGATCCAGAGAGGAAGGACTGACAAGAAGGAATTATTCAGA  1579
 458  Leu Lys Val ***                                                462

1580  AAAACACTGACAGATGTTTTATAAATTGTACAGAAAAATAGTTAAAAATGCAATAGGTTG  1639
1640  AAGTTTGGAGATATGTTTCTCTCTGAAATTACTGTGAATATTAACAAACACTTACTTG    1699
1700  ATCTATGTTATGAAATAAGTAGCAACTTCCCTTGCCAGCAAATGTCTTGTACCTTTCTAAAGT 1759
1760  GTATTTCTGATGTGAACTTCCCCCTTACTTGCTAGGTTTCATAATTAAAAGACTG       1819
1820  GTATTTAAAAGAGTCAAACACTATAAAATGAGTAAGTTGACGATGTTTTAAGATTGCACC  1879
1880  TGGCAGTGTGCCTTTTTATGCAAGGCACACTTCTCCCTGCACTTCAGTCAGTTCTGCTTCCTCGAGCTGCTTTTAATTTTA 1939
1940  GCAAAATGTTTTCTAAAGGGCTTAGTTGGATTTAAAAAAAAAAAAAAAA              1999
2000  AGTCTGGAGTACTTTCTAAAGGGCTTAGTTGGATTTAAAAAAAAAAAAAAAA          2050
```

FIG. 3

```
                                        Met Leu Glu Leu Arg His Arg Gly    8
Ser Cys Pro Gly Pro Arg Glu Ala Val Ser Pro Pro His Arg Glu   23
Gly Glu Ala Ala Gly Gly Asp His Glu Thr Glu Ser Thr Ser Asp   38
Lys Glu Thr Asp Ile Asp Asp Arg Tyr Gly Asp Leu Asp Ser Arg   53
Thr Asp Ser Asp Ile Pro Glu Ile Pro Pro Ser Ser Asp Arg Thr   68
Pro Glu Ile Leu Lys Lys Ala Leu Ser Gly Leu Ser Ser Arg Trp   83
Lys Asn Trp Trp Ile Arg Gly Ile Leu Thr Leu Thr Met Ile Ser   98
Leu Phe Phe Leu Ile Ile Tyr Met Gly Ser Phe Met Leu Met Leu  113
Leu Val Leu Gly Ile Gln Val Lys Cys Phe His Glu Ile Ile Thr  128
Ile Gly Tyr Arg Val Tyr His Ser Tyr Asp Leu Pro Trp Phe Arg  143
Thr Leu Ser Trp Tyr Phe Leu Leu Cys Val Asn Tyr Phe Phe Tyr  158
Gly Glu Thr Val Ala Asp Tyr Phe Ala Thr Phe Val Gln Arg Glu  173
```

FIG. 3 (cont'd)

| 188 | 203 | 218 | 233 | 248 | 263 | 278 | 293 | 308 | 323 | 338 | 353 |
|-----|-----|-----|-----|-----|-----|-----|-----|-----|-----|-----|-----|
| Phe | Val | His | Gln | Ser | Phe | Glu | Ile | Val | Pro | Leu | Gln |
| Ser | Leu | Thr | Ile | Ser | Phe | Trp | Phe | Cys | Glu | Phe | Phe |
| Ile | Ser | Ala | Val | Ile | Ser | Lys | Gly | Val | Cys | Pro | Pro |
| Phe | Leu | Trp | Leu | Pro | Phe | Thr | Phe | Phe | Pro | Phe | Tyr |
| Arg | Val | Met | His | Val | Leu | Val | Val | Val | Glu | Leu | Val |
| Tyr | Cys | Tyr | Ser | Pro | Tyr | Pro | Tyr | Phe | Cys | Ser | Ser |
| His | Met | Phe | Gln | Ile | Leu | Lys | Gln | Val | Thr | Tyr | Val |
| Arg | Phe | Gln | Ser | Trp | Phe | Ser | Tyr | Asn | Glu | Thr | Arg |
| Ile | Cys | Phe | His | Phe | Gly | Leu | Ser | Ser | Thr | Ser | Val |
| Leu | Gly | Gln | Thr | Met | Asp | Pro | Gly | Val | Thr | Tyr | Leu |
| Phe | Ala | Leu | Val | Ile | Thr | Leu | Phe | Leu | Gln | Phe | Tyr |
| Leu | Tyr | Arg | Thr | Gly | Pro | Ile | Gly | Ala | Ser | Leu | Ser |
| Gln | Leu | His | Leu | Glu | Asn | Cys | Ile | Ala | Arg | Phe | Arg |
| Leu | Tyr | Lys | Val | Asn | Val | Gly | Phe | Ala | Glu | Ser | Val |
| Glu | Ala | Lys | Val | Asn | Val | Gly | Phe | Ala | Ser | Lys | Lys |

FIG. 3 (cont'd)

```
Ile His Ser Ile Ala Leu Ser Thr Phe Ala Ser Leu Ile Gly Pro   368
Phe Gly Gly Phe Phe Ala Ser Gly Phe Lys Arg Ala Phe Lys Ile   383
Lys Asp Phe Ala Asn Thr Ile Pro Gly His Gly Gly Ile Met Asp   398
Arg Phe Asp Cys Gln Tyr Leu Met Ala Thr Leu Val His Gly Tyr   413
Ile Thr Ser Phe Ile Arg Gly Pro Asn Pro Ser Lys Val Leu Gln   428
Gln Leu Leu Val Leu Gln Pro Glu Gln Leu Asn Ile Tyr Lys       443
Thr Leu Lys Thr His Leu Ile Glu Lys Gly Ile Leu Gln Pro Thr   458
Leu Lys Val ***                                               461
```

FIG. 4

```
                 10         20         30         40         50
Human       1  MLELRHRGSC PGPREAVSPP HREGEAAGGD HETESTSDKE TDIDDRYGDL
Drosophila  1  MAEVRRR--- ---------- ---------- KGEDEPLEDT VDSEEKIPE
Yeast       1  MSD------- ---------- ---------- ---NPEMKP HGTS-KEIVE SVTDATSKAI
E. coli     1  MLAAWEW--- ---------- ---------- ---------- ----------

60         70         80         90        100
Human       51 DSRTDSDIPE IPPSSDRTPE ILKKALSGLS SRWKNWWIRG ILT--LTMIS
Drosophila  51 EKFVDELAKN LPQGTDKTPE ILDSALKDLP DRWKNWVIRG IFTW--IMIC
Yeast       51 DKLQEELHKD ASESV--TPV TKESTAATKE SRKYNFFIRT V--WTFVMIS
E. coli     51 ----GQLS-- ---------- ---------- ----GFTTRS QRVW-LAVLC 110        120        130        140        150
Human      101 LFFLIIYMGS FMLMLLVLGI QVKCFHEIIT IGYRVYHSYD LPWFRTLSWY
Drosophila 101 GFALIIYGGP LALMITTLLV QVKCFQEIIS IGYQVYRIHG LPWFRSLSWY
Yeast      101 GFFITLASGH AWCIVLILGC QIATFKECIA VTSASGREKN LPLTKTLNWY
E. coli    101 GLLLAL---- ---------- MLF LLPEYHRNIH QP----LVE ISLWASLGWW 160        170        180        190        200
Human      151 FLLCV--NYF FYGETVADYF ATFVQREEQL QFLIRYHRFI SFALYLAGFC
Drosophila 151 FLL--TSNYF FYGENLVDYF GVVINRVEYL KFLVTYHRFL SFALYIIGFV
Yeast      151 LLF--TTIYY LDGKSLFKFF QATFYEYPVL NFIVTNHKFI CYCLYLMGFV
E. coli    151 IVALLLVLFY PGSAAIWR-- ----NSKTL RLIFG---- ---VLTIVPFF
```

FIG. 4 (cont'd)

```
                      210        220        230        240        250
Human        201 MEVLSLVKEH YRLQFYMFAW THVTLLITVT QSHLVIQNLF EGMIWFLVPI
Drosophila   201 WFVLSLVKKY YIKQFSLFAW THVSLLIVVT QSYLIQNIF  EGLIWFIVPV
Yeast        201 LFVCSLRKGF LKFQFGSLCV THMVLLLVVF QAHLIKNVL  NGLFWFLLPC
E. coli      201 WGMLALRA-- --WHYD---- ---------- ----ENHY   SGAIWLLYVM 260        270        280        290        300
Human        251 SSVICNDITA YLFGFEFGRT PLI-KLSPKK TWEGFIGGFF STVVFGFIAA
Drosophila   251 SMIVCNDVMA YVFGFEFGRT PLI-KLSPKK TWEGFIGGGF ATVLFGILFS
Yeast        251 GLVIVNDIFA YLCGITFGKT KLIE-ISPKK TLEGFLGAWF FTALASIILT
E. coli      251 ILVWGADSGA YMFGKLFGKH KLAPKVSPGK TWQGFIGG-- -----LAT 310        320        330        340        350
Human        301 YVLSKYQYFV CPVEYRSDVN SFVTECEPSE LFQLQTYSLP PFLKAVLRQE
Drosophila   301 YVLCNYQYFI CPIQYSEEQG RMTMSCVPSY LFTPQEYSLK LFGIG----K
Yeast        301 RILSPYTYLT CPVEDLHTNF FSNLTCELNP VFLPQVYRLP PIFFDKVQIN
E. coli      301 AAVISWGYGM ---------- ---------- ---------- ---WANLDVA 360        370        380        390
Human        351 RVSLYPFQIH SIALSTFASL IGPFGGFFAS GFKRAFKIKD FANTIPGHGG
Drosophila   351 TLNLYPFIWH SISLSLFSSI IGPFGGFFAS GFKRAFKIKD FGDMIPGHGG
Yeast        351 SITVKPIYFH ALNLATFASL FAPFGGFFAS GLKRTFKVKD FGHSIPGHGG
E. coli      351 PVTL------ -LICSIVAAL ASVLGDLTES MFKREAGIKD SGHLIPGHGG
```

*FIG. 4 (cont'd)*

```
              410          420          430          440          450
Human      401 IMDREDCQYL   MATLVHGYIT   SFI---RGPN   PSKVLQQLLV   LQPEQQLNIY
Drosophila 401 IMDREDCQFL   MATFVNVY--   --ISFIRTPS   PAKLLTQIYN   LKPD------
Yeast      401 ITDRVDCQFI   MGSFANLYYE   TFISEHRITV   DTVLSTILMN   LNDKQIIELI
E. coli    401 ILDRIDS---   ----------   ---LTA----   AVPVFACLLL   L---------

460          470          480          490          500
Human      451 KTLKTHLIEK   GI--------   LQPTLKV---   ----------   ----------
Drosophila 451 ----------   --QQYQIYQS   ------LKD   NLGHMLT...   ..........
Yeast      451 DILIRFLSKK   GIISAKNEEK   LADIFNVTKK   SLTNHS*...   ..........
E. coli    451 ----------   ----------   ---VERTL*-   ----------   ----------
```

MAMMALIAN CDP-DIACYLGLYCEROL SYNTHASE

TECHNICAL FIELD OF THE INVENTION

This present invention provides cDNA sequences and polypeptides having the enzyme CDP-diacylglycerol synthase (CDS) activity. CDS is also known as CTP:phosphatidate cytidylyltransferase (EC2.7.7.41). The present invention further provides for isolation and production of polypeptides involved in phosphatidic acid metabolism and signaling in mammalian cells, in particular, the production of purified forms of CDS.

BACKGROUND OF THE INVENTION

CDP-diacylglycerol (DAG) is an important branch point intermediate just downstream of phosphatidic acid (PA) in the pathways for biosynthesis of glycerophosphate-based phospholipids (Kent, *Anal. Rev. Biochem.* 64: 315–343, 1995). In eukaryotic cells, PA, the precursor molecule for all glycerophospholipid, is converted either to CDP-DAG by CDP-DAG synthase (CDS) or to DAG by a phosphohydrolase. In mammalian cells, CDP-DAG is the precursor to phosphatidylinositol (PI), phosphatidylglycerol (PG), and cardiolipin (CL). Diacylglycerol is the precursor to triacylglycerol, phosphatidylethanolamine, and phosphatidylcholine in eukaryotic cells. Therefore, the partitioning of phosphatidic acid between CDP-diacylglycerol and diacylglycerol must be an important regulatory point in eukaryotic phospholipid metabolism (Shen et al., *J. Biol. Chem.* 271:789–795, 1996). In eukaryotic cells, CDP-diacylglycerol is required in the mitochondria for phosphatidylglycerol and cardiolipin synthesis and in the endoplasmic reticulum and possibly other organelles for the synthesis of phosphatidylinositol (PI). PI, in turn, is the precursor for the synthesis of a series of lipid second messengers, such as phosphatidylinositol-4,5-bisphosphate ($PIP_2$), DAG and inositol-1,4,5-trisphosphate ($IP_3$). Specifically, $PIP_2$ is the substrate for phospholipase C that is activated in response to a wide variety of extracellular stimuli, leading to the generation of two lipid second messengers; namely, DAG for the activation of protein kinase C and $IP_3$ for the release of $Ca^{++}$ from internal stores (Kent, *Anal. Rev. Biochem.* 64: 315–343, 1995).

The genes coding for CDS have been identified in *E. coli* (Icho et al, *J. Biol. Chem.* 260:12078–12083, 1985), in yeast (Shen et al., *J. Biol. Chem.* 271:789–795, 1996), and in Drosophila (Wu et al., *Nature* 373:216–222, 1995). The cloning of a mammalian version of CDS has not been reported. It is of interest to isolate the cDNAs coding for human CDS and express it in mammalian cells to determine the potential roles of this enzyme in cellular function and to use this enzyme as a target for the development of specific compounds that are modulators of its activity. With the advance in the understanding of disease processes, it has been found that many diseases result from the malfunction of intracellular signaling. This recognition has led to research and development of therapies based on the interception of signaling pathways in diseases (Levitzki, *Curr. Opin. Cell Biol.* 8:239–244, 1996). Compounds that would modulate CDS activity, and hence generation of a variety of lipid second messengers and modulate the signals involved in cell activation, may be of therapeutic interest in the areas of inflammation and oncology. This patent is based upon the cloning and expression of a human CDS cDNA.

SUMMARY OF THE INVENTION

The present invention provides a cDNA sequence, polypeptide sequence, and transformed cells for producing isolated recombinant mammalian CDS. The present invention provides a novel human polypeptide and fragment thereof, having CDS activity. The polypeptide discovered herein is novel and will be called hCDS. CDS catalyzes the conversion of phosphatidic acid (PA) to CDP-diacylglycerol (CDP-DAG), which in turn is the precursor to phosphatidylinositol (PI), phosphatidylglycerol (PG) and cardiolipin (CL).

The present invention further provides nucleic acid sequences coding for expression of the novel CDS polypeptides and active fragments thereof. The invention further provides purified CDS mRNA's and antisense oligonucleotides for modulation of expression of the genes coding for CDS polypeptides. Assays for screening test compounds for their ability to modulate CDS activity are also provided.

Recombinant CDS is useful for screening candidate drug compounds that modulate CDS activity, particularly those compounds that activate or inhibit CDS activity. The present invention provides cDNA sequences encoding a polypeptide having CDS activity and comprising the DNA sequence set forth in SEQ ID NO. 1, shortened fragments thereof, or additional cDNA sequences which due to the degeneracy of the genetic code encode a polypeptide of SEQ ID NO. 2 or biologically active fragments thereof or a sequence capable of hybridizing thereto under high stringency conditions. The present invention further provides a polypeptide having CDS activity and comprising the amino acid sequence of SEQ ID NO. 2 or biologically active fragments thereof.

Also provided by the present invention are vectors containing a DNA sequence encoding a mammalian CDS enzyme in operative association with an expression control sequence. Host cells, transformed with such vectors for use in producing recombinant CDS are also provided with the present invention. The inventive vectors and transformed cells are employed in a process for producing recombinant mammalian CDS. In this process, a cell line transformed with a cDNA sequence encoding a CDS enzyme in operative association with an expression control sequence, is cultured. The claimed process may employ a number of known cells as host cells for expression of the CDS polypeptide, including, for example, mammalian cells, yeast cells, insect cells and bacterial cells.

Another aspect of this invention provides a method for identifying a pharmaceutically-active compound by determining if a selected compound is capable of modulating the activity of CDS for converting PA to CDP-DAG. A compound capable of such activity is capable of modulating signaling kinase pathways and being a pharmaceutical compound useful for augmenting trilineage hematopoiesis after cytoreductive therapy and for anti-inflammatory activity in inhibiting the inflammatory cascade following hypoxia and reoxygenation injury (e.g., sepsis, trauma, ARDS, etc.).

The present invention further provides a transformed cell that expresses active mammalian CDS and further comprises a means for determining if a drug candidate compound is therapeutically active by modulating recombinant CDS activity.

BRIEF DESCRIPTION OF THE DRAWINGS

FIG. 1 shows the cDNA sequence encoding hCDS. The nucleotide sequence analysis and restriction mapping of the cDNA clone revealed a 5'-untranslated region of 149 base pairs, an open reading frame capable of encoding a 461 amino acid polypeptide that spans nucleotide positions 150 to 1535 and a 3'-untranslated region of 520 base pairs.

FIG. 2 shows the translated amino acid sequence of human CDS.

FIG. 3 shows the amino acid sequence of human CDS.

FIG. 4 shows the sequence homology among the human CDS coding sequence, the yeast CDS coding sequence, E. coli CDS coding sequence, and the Drosophila CDS coding sequence. This comparison shows that human CDS has the greatest extended homology with amino acids 109 to 448 of Drosophila CDS. The human CDS protein and the CDS protein from Drosophila, yeast, and E. coli have 45%, 21% and 7% overall match in amino acid sequence, respectively.

FIG. 6 confirms that the radiolabeled product found in the membrane fractions does migrate with a CDP-DAG standard on TLC. The identities of labeled bands were determined by migration of phospholipid standards visualized by UV or FL imaging on the STORM after primulin staining. Lanes 1–3 represent triplicate samples derived from membranes of NCI-H460 cells transfected with the CDS expression vector, and lanes 4–6 represent triplicate samples from transfectants with the control vector. Cells transfected with the human CDS cDNA showed 1.6–2.4 fold more CDS activity in membrane fractions than vector transfectants. The relative CDS activity between CDS transfectants and vector transfectants was similar when determined by scintillation counting or TLC analysis. These data indicate that the human cDNA clone of SEQ ID NO. 1 does encode CDS activity.

DETAILED DESCRIPTION OF THE INVENTION

Figure 5:
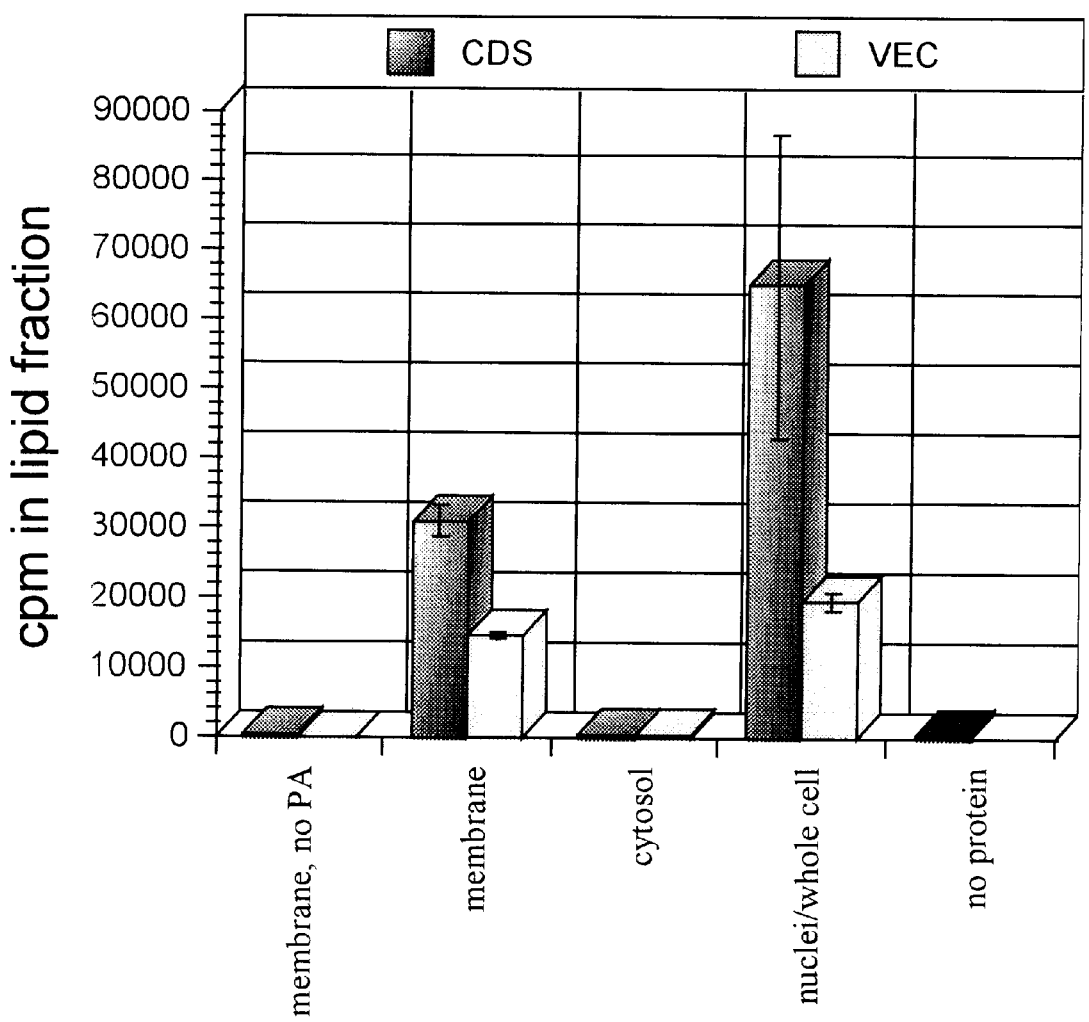
FIG. 5 shows the results of in vitro CDS activity assays on cell fractions from stable transfectants of NCI-H460 cells. CDS activity was assessed by conversion of ($\alpha$-$^{32}$P) CTP to ($^{32}$P)CDP-DAG in in vitro reactions that required addition of an exogenous PA substrate. This is a representative histogram comparing the radiolabel incorporated into various cell fractions (membranes, cytosol, and nuclei/unbroken cells) from NCI-H460 cells stably transfected with the CDS cDNA (pCE2.hCDS) or vector only (pCE2). In all fractions, the CDS cDNA increased radiolabel in the organic phase of the reactions. Total CDS activity was much greater in membrane fractions, as would be expected for membrane associated CDS, compared to cytosol fractions. Activity in unbroken cells masked the activity specific to nuclei.

The present invention provides novel, isolated, biologically active mammalian CDS enzymes. The term "isolated" means any CDS polypeptide of the present invention, or any other gene encoding CDS polypeptide, which is essentially free of other polypeptides or genes, respectively, or of other contaminants with which the CDS polypeptide or gene might normally be found in nature.

The invention includes a functional polypeptide, CDS, and functional fragments thereof. As used herein, the term "functional polypeptide" refers to a polypeptide which possesses a biological function or activity which is identified through a biological assay, preferably cell-based, and which results in the formation of CDS-DAG species from PA. A "functional polynucleotide" denotes a polynucleotide which encodes a functional polypeptide. Minor modification of the CDS primary amino acid sequence may result in proteins which have substantially equivalent activity as compared to the sequenced CDS polypeptide described herein. Such modifications may be deliberate, as by site-directed mutagenesis, or may be spontaneous. All of the polypeptides produced by these modifications are included herein as long as the activity of CDS is present. This can lead to the development of a smaller active molecule which would have broader utility. For example, it is possible to remove amino or carboxy terminal amino acids which may not be required for CDS activity.

The CDS polypeptide of the present invention also includes conservative variations of the polypeptide sequence. The term "conservative variation" denotes the replacement of an amino acid residue by another, biologically active similar residue. Examples of conservative variations include the substitution of one hydrophobic residue, such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of parent amino acid provided that antibodies raised to the substituted polypeptide also immunologically react with the unsubstituted polypeptide.

The present invention further includes allelic variations (naturally-occurring base changes in the species population which may or may not result in an amino acid change) of the DNA sequences herein encoding active CDS polypeptides and active fragments thereof. The inventive DNA sequences further comprise those sequences which hybridize under stringent conditions (see, for example, Maniatis et al, Molecular Cloning (A Laboratory Manual), Cold Spring Harbor Laboratory, pages 387–389, 1982) to the coding region (e.g., nucleotide #150 to nucleotide #1535 in SEQ ID NO. 1). One such stringent hybridization condition is, for example, 5× SSC at 65° C., followed by washing in 0.1× SSC at 65° C. for thirty minutes. Alternatively, another stringent hybridization condition is 50% formamide, 5× SSC at 42° C. The present invention further includes DNA sequences which code for CDS polypeptides having CDS activity but differ in codon sequence due to degeneracy of the genetic code. Variations in the DNA sequences which are caused by point mutations or by induced modifications of the sequence of SEQ ID NO. 1, which enhance the activity of the encoded polypeptide or production of the encoded CDS polypeptide are also encompassed by the present invention.

CDS Sequence Discovery

A homology search of the Genbank database (Boguski, et al., Science 265:1993–1994, 1994) of expressed sequence tags (dbEST) using Drosophila CDS protein sequence as a probe came up with several short stretches of cDNA sequence with homology to the Drosophila CDS protein sequence. These cDNA sequences were derived from single-run partial sequencing of random human cDNA clones carried out mainly by I.M.A.G.E. Consortium [LLNL] cDNA clones program. An example of the amino acid sequence homology between the Drosophila CDS and a human cDNA clone (IMAGE Clone ID #135630) is shown below:

371 KRAFKIKDFGDMIPGHGGIMDRFDCQFL-
    MATFVNVYIS    408    KRAFKIKDF+
    IPGHGGIMDRFDCQ+LMATFV+VYI+

11 KRAFKIKDFANTIPGHGGIMDRFDCQYL-
    MATFVHVYIT 124

The top line (SEQ ID NO. 3) refers to the Drosophila CDS sequence from amino acids 371 to 408 and the bottom line (SEQ ID NO. 4) refers to a homologous region from IMAGE Clone ID #135630 translated using reading frame +2. Identical amino acids between these two sequences are shown on the middle line with the "+" signs indicating conservative amino acid changes. In order to determine if such cDNA clones with this level of homology to the Drosophila CDS sequence encoded human CDS sequence, it was necessary to isolate the full-length cDNA clone, insert it into an expression vector, and test if cells transfected with the cDNA expression vector will produce more CDS activity.

Accordingly, a synthetic oligonucleotide (o.h.cds.1R), 5'-CCCACCATGG CCAGGAATGG TATTTGC -3' (SEQ ID NO. 5), was made based on the complement sequence of the amino acid region, ANTIPGHGG, of IMAGE Clone ID #135630 for the isolation of a putative human cDNA clone from a SuperScript human leukocyte cDNA library (Life Technologies, Gaithersburg, Md.) using the GeneTrapper cDNA positive selection system (Life Technologies, Gaithersburg, Md.). The colonies obtained from positive selection were screened with a [γ-$^{32}$P]-ATP labeled synthetic oligonucleotide (o.h.cds.1), 5'-AGTGATGTGA ATTCCT-TCGT GACAG-3' (SEQ ID NO. 6), corresponding to nucleotides 144–168 of IMAGE Clone ID #133825. Of the few cDNA clones that hybridized with the o.h.cds.1 probe, clone LK64 contained the largest cDNA insert with a size of 1700 base pairs. DNA sequence analysis of LK64 showed the translated sequence of its largest open reading frame from the 5' end contained extensive homology with amino acids 109 to 448 of the Drosophila CDS protein sequence. Clone LK64 did not appear to contain a full-length cDNA insert for CDS. It was missing the coding region corresponding to the first 110 amino acids from the N-terminus. A second homology search of the Genbank database (Boguski, et al., *Science* 265:1993–1994, 1994) using the 3'-untranslated sequence of LK64 as a probe came up with more short stretches of cDNA sequences with perfect homology to the 3' end of the putative human CDS clone LK64. Restriction mapping and DNA sequence analysis of IMAGE Clone ID #145253 (Genome Systems, St. Louis, Mo.), derived from a placental cDNA library, showed it contained extensive sequence homology with the N-terminal coding region of the Drosophila CDS and overlapped with the sequence obtained from clone LK64.

To assemble the putative full-length human CDS cDNA clone, a 500 base pair Pst I-Nco I fragment from of IMAGE Clone ID #145253 and a 1500 base pair Nco I-Not I fragment from LK64 were isolated. These two fragments were inserted into a Pst I and Not I digested vector pBluescriptII SK(-) vector via a three-part ligation to generate pSK.hcds.

FIG. 1 shows the DNA sequence ID of the putative human cDNA of CDS. The nucleotide sequence analysis and restriction mapping of the cDNA clone revealed a 5'-untranslated region of 149 base pairs, an open reading frame encoding a 461 amino acids polypeptide that spans nucleotide positions 150 to 1535 and a 3'-untranslated region of 520 base pairs (FIG. 2). The ATG initiation site for translation was identified at nucleotide positions 150–152 and fulfilled the requirement for an adequate initiation site. (Kozak, *Critical Rev. Biochem. Mol. Biol.* 27:385–402, 1992). There was another upstream ATG at positions 4–6 but it was followed by an in-phase stop codon at positions 19–20. The calculated molecular weight of CDS is 53,226 daltors with a predicted pI of 7.57.

The sequence of the 461 amino acid open reading frame (FIG. 3) was used as the query sequence to search for homologous sequences in protein databases. A search of Genbank Release 92 from the National Center for Biotechnology Information (NCBI) using the BLAST program showed that this protein was most homologous to the Drosophila CDS, the yeast CDS, and the *E. coli* CDS. FIG. 4 shows amino acid sequence alignment of this putative human CDS coding sequence with the Drosophila CDS, the yeast CDS, and the *E. coli* coding sequences, showing that the human CDS is most homologous to the Drosophila CDS. Expression of Human CDS cDNA in Mammalian Cells To see if overexpression of human CDS would have any effect on mammalian cells, the entire cDNA insert (~2,000 base pairs) from pSK.hcds was cleaved with Asp718 I and Not I for insertion into the mammalian expression vector pCE2 to generate pCE2.hCDS. The plasmid pCE2 was derived from pREP7b (Leung et al. *Proc. Natl. Acad. Sci. USA*, 92:4813–4817, 1995) with the RSV promoter region replaced by the CMV enhancer and the elongation factor-1α (EF-1α)promoter and intron. The CMV enhancer came from a 380 base pair Xba I-Sph I fragment produced by PCR from pCEP4 (Invitrogen, San Diego, Calif.) using the primers 5'-GGCTCTAGAT ATTAATAGTA ATCAATTAC-3' (SEQ ID NO. 7) and 5'-CCTCACGCAT GCACCATGGT AATAGC-3' (SEQ ID NO. 8). The EF-1α promoter and intron (Uetsuki et al., *J. Biol. Chem.*, 264:5791–5798, 1989) came from a 1200 base pair Sph I-Asp718 I fragment produced by PCR from human genomic DNA using the primers 5'-GGTGCATGCG TGAGGCTCCG GTGC-3' (SEQ ID NO. 9) and 5'-GTAGTTTTCA CGGTACCTGA AATGGAAG-3' (SEQ ID NO. 10). These 2 fragments were ligated into a Xba I/Asp718 I digested vector derived from pREP7b to generate pCE2.

A second clone, pCE2.hCDS2, was constructed that lacked the human CDS 3'-UT region (520 nt). An Asp718 I (in the multiple cloning site)/NcoI fragment and a NcoI/BamHI fragment from pSK.hCDS were combined in a three-part ligation with Asp718 I/BamHI digested pCE2. Northern blot analysis of 293-EBNA human embryonic kidney cells transiently transfected with CDS cDNA expression plamids (pCE2.hCDS or pCE2.hCDS2) showed that deletion of the entire 3'-UT region had little effect on CDS steady-state mRNA levels.

The CDS activity in transfected cell fractions (membranes, cytosol, nuclei/unbroken cells) was determined by incorporation of ($\alpha$-$^{32}$P)CTP into ($^{32}$P)CDP-DAG in the presence of exogenously added PA substrate. Cells were fractionated by resuspending previously frozen cell pellets in cold hypotonic lysis buffer (HLB; 10 mM KCl, 1.5 mM $MgCl_2$, 10 mM Tris, pH 7.4, 2 mM benzamidine HCl, and 10 μg/ml each leupeptin, soybean trypsin inhibitor, and pepstatin A) at approx. 5×10$^7$ cells/ml. After 10 min. on ice, cells were dounced (Wheaton pestle A) 40 strokes, then spun 500×g, 10 min. at 4° C. to remove nuclei and unbroken cells. The resuspension of the pellet, incubation, and low speed spin were repeated twice. The final "nuclei/unbroken cells" pellet was resuspended in 50–100 μl HLB. Supernatants were spun at 109,000×g, 30 min. at 4° C. generating "cytosol" supernates and "membrane" pellets. The pellets were resuspended in 150–225 μl HLB. An aliquot of each fraction was removed for determination of protein concentration by a BCA assay. Fractions were stored at −70° C. All assays were done on fractions after one thaw.

The in vitro CDS activity assay conditions were a modification of methods described previously (Mok et al., FEBS Letters 312:236–240,1992; and Wu et al., Nature 373:216–222,1995). Briefly, each 0.3 ml reaction combined 0.23 mM PA (Sigma; from egg yolk lecithin), 50 mM Tris-maleate, pH 7.0, 1.5% Triton X-100, 0.5 mM DTT, 75–500 µg protien from cell fractions, 30 mM $MgCl_2$, and 2 µCi ($\alpha$-$^{32}$P)CTP. $MgCl_2$ and ($\alpha$-$^{32}$P)CTP were added just prior to a 10 min. incubation at 37° C. The reactions were terminated with 4 ml chloroform:methanol (1:1) and vortexing. The organic phase was extracted three times with 1.8 ml 0.1N HCl with 1 M NaCl, and vortexing. Radioactivity in the organic phase was determined by scintillation counting or TLC.

A flip-flop TLC (ffTLC) system (Gruchalla et al., *J. Immunol.* 144:2334–2342, 1990) was modified for the separation of CDP-DAG and PA. Specifically, 200 ml of organic phase was dried and brought up in 20 µL $CHCl_3$:MeOH (2:1) and spotted in the center of a 20×20 cm TLC plate (Analtech Silica Gel HP-HLF). TLC was run in $CHCl_3$:MeOH:$NH_4OH$:$H_2O$ (65:30:4:1) until the solvent had reached the top of the plate. In this solvent system, neutral and cationic lipids migrate, whereas PA, CDP-DAG and other anionic lipids stay near the origin. The plate was dried and visualized by UV with 0.05% primulin stain (Sigma, St. Louis, Mo.) in 80% acetone. The plate was cut below the PC standard, and the bottom half of the plate was rotated 180° and run in $CHCl_3$:MeOH:Acetic Acid:$H_2O$ (80:25:15:5) to enable migration of the anionic lipids until the solvent reached the top of the plate. The radioactive bands on the TLC plate were quantified using a STORM® phosphorimager (Molecular Dynamics, Sunnyvale, Calif.). Non-radiolabeled lipid standards were stained with primulin and visualized by flourescence using the STORM®.

FIG. 5 shows the results of in vitro CDS activity assays on cell fractions from stable transfectants of NCI-H460 cells. CDS activity was assessed by conversion of ($\alpha$-$^{-}$P) CTP to ($^{-}$P)CDP-DAG in in vitro reactions that required addition of an exogenous PA substrate. This is a representative histogram comparing the radiolabel incorporated into various cell fractions (membranes, cytosol, and nuclei/unbroken cells) from NCI-H460 cells stably transfected with the CDS cDNA (pCE2.hCDS) or vector only (pCE2). In all fractions, the CDS cDNA increased radiolabel in the organic phase of the reactions. Total CDS activity was much greater in membrane fractions, as would be expected for membrane associated CDS, compared to cytosol fractions. Activity in unbroken cells masked the activity specific to nuclei.

Figure 6:
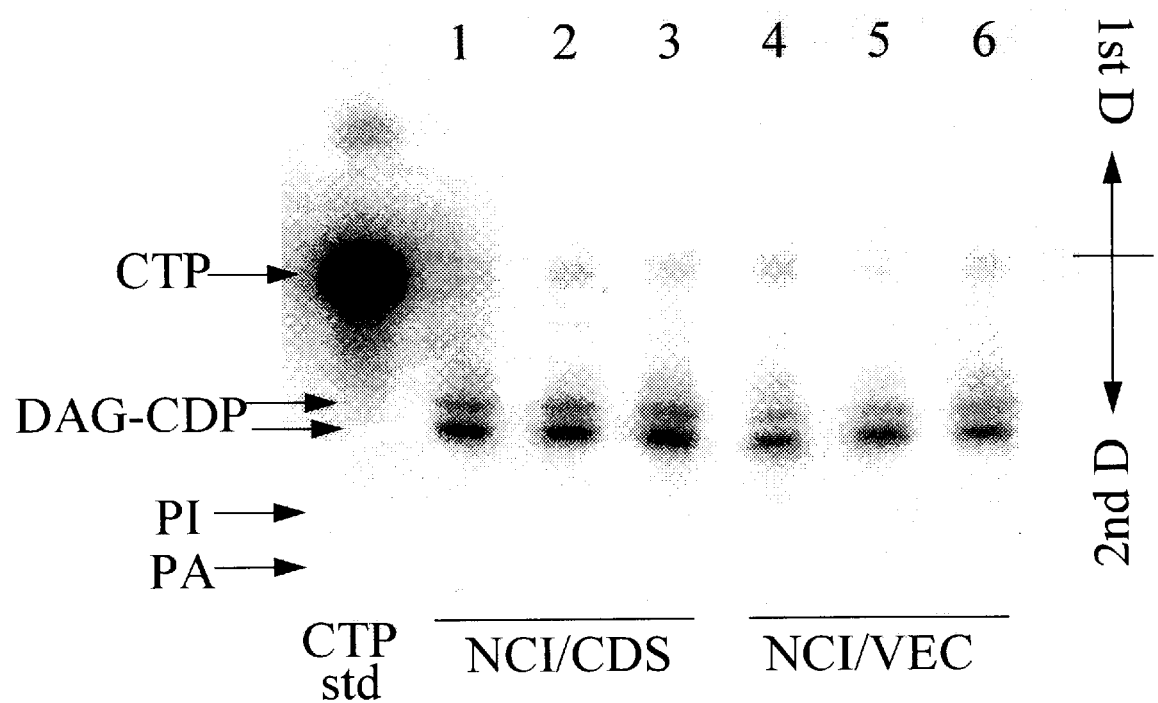
FIG. 6 is a representative phosphorimage of [$^{32}$P] phospholipids from membrane fraction CDS assay reactions after the second dimension of ffTLC.

FIG. 6 is a representative phosphorimage of [$^{32}$P] phospholipids from membrane fraction CDS assay reactions after the second dimension of ffTLC. FIG. 6 confirms that the radiolabeled product found in the membrane fractions does migrate with a CDP-DAG standard on TLC. The identities of labeled bands were determined by migration of phospholipid standards visualized by UV or FL imaging on the STORM after primulin staining. Lanes 1–3 represent triplicate samples derived from membranes of NCI-H460 cells transfected with the CDS expression vector, and lanes 4–6 represent triplicate samples from transfectants with the control vector. Cells transfected with the human CDS cDNA showed 1.6–2.4 fold more CDS activity in membrane fractions than vector transfectants. The relative CDS activity between CDS transfectants and vector transfectants was similar when determined by scintillation counting or TLC analysis. Similar CDS activity was seen in two different transfected human cell lines, NCI-H460 and ECV304. The average specific activity of CDS in membranes of CDS transfectants was 2.7 fmol/min/mg protein compared to 1.4 fmol/min/mg protein in membranes of vector transfectants. These results demonstrated that overexpression of the human CDS cDNA clone lead to an increase in CDS activity in cell fractions and that activity in an in vitro assay was completely dependent on the addition of PA. These data indicate that the human cDNA clone of SEQ ID NO. 1 does encode CDS activity.

Complementation of Yeast cds1 Mutant with Human CDS

As the yeast CDS gene is essential for growth (Shen et al., *J. Biol. Chem.* 271:789–795, 1996), another way to show that the cDNA does encode CDS activity was to determine if the human CDS cDNA will complement the growth defect of a mutant yeast strain with a deletion in the endogenous yeast CDS gene. Accordingly, the human CDS cDNA was cloned downstream of a GAL1 promoter in a yeast expression vector. Specifically, a Hind III-Sac I fragment from pSK.hCDS was inserted into pYES.LEU vector to generate pYES.hCDS. pYES.LEU was derived from pYES2 (Invitrogen, San Diego, Calif.) by inserting a BspH I fragment containing a LEU2 marker from pRS315 (Sikorski et al., *Genetics* 122:19–27, 1989) into the Nco I of pYES2. pYES.hCDS was introduced into a null cdsl strain of yeast, YSD90A (Shen et al., *J. Biol. Chem.* 271:789–795, 1996), with a covering plasmid, pSDG1, carrying the functional yeast CDS1. The latter plasmid was cured from cells by growth in media lacking leucine but containing uracil and galactose. PCR analysis confirmed the absence of the yeast CDS1 gene and Northern blot analysis verified expression of the human CDS cDNA. This strain was found to be absolutely dependent on galactose for growth. Galactose activates the GAL1 promoter for the production of human CDS protein. When the carbon source was switched to glucose, which would shut down the GAL1 promoter, growth stopped totally in less than a generation. These data show the human CDS was able to complement the growth defect of a yeast cdsl mutant.

The cells grown on galactose were lysed and assayed for CDS activity according to the assay method described (Shen et al., *J. Biol. Chem.* 271:789–795, 1996). The specific activity using yeast conditions showed activity at 20% of single copy CDS1 wild type activity. This is consistent with the above plasmid in a wild type background showing pproximately 1.3 fold increase in activity when grown on galactose versus glucose.

Figure 7A:
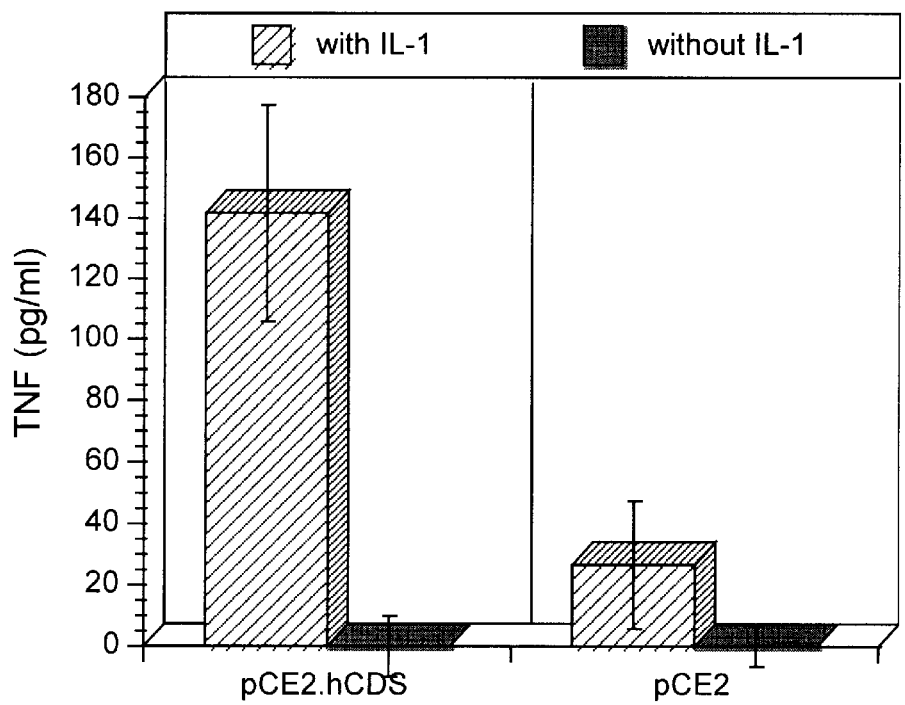
FIG. 7 shows that production of TNF-$\alpha$ (tumor necrosis factor alpha) and IL-6 in ECV304 cells stably transfected with a CDS expression vector increases by greater than five fold relative to ECV304 cells stably transfected with control vector after equal stimulation with IL-1$\beta$ (interleukin-1 beta). There was little effect on basal level of cytokine release. These data indicate that overexpression of CDS amplified the cytokine signaling response in these cells, as opposed to enhancing steady state, basal signals.
Figure 7B:
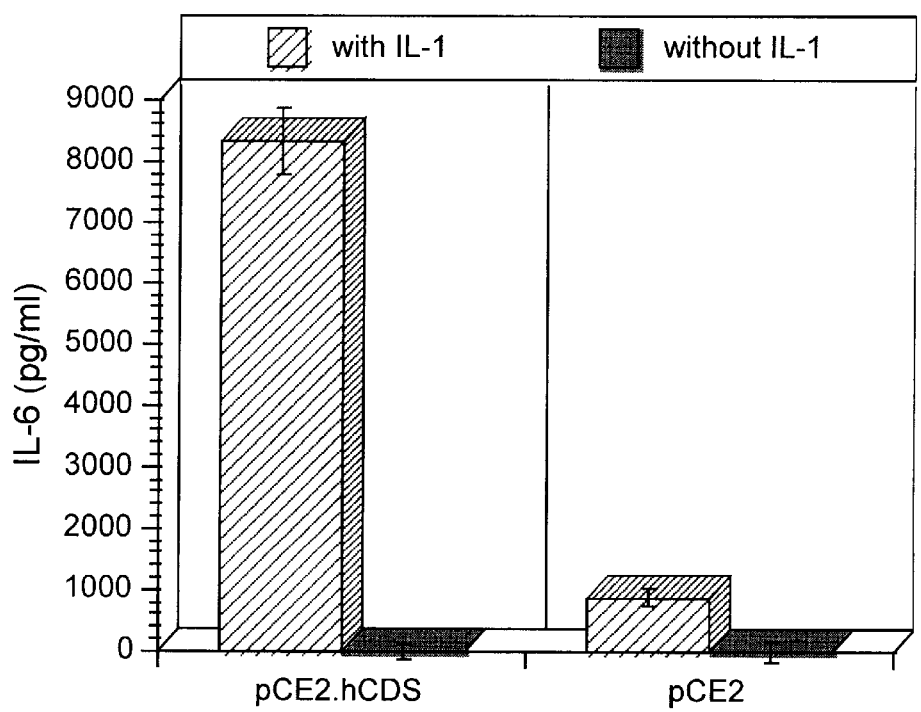

The following experiment found that CDS overexpression enhanced cytokine induced signaling in cells. Over-expression of CDS was expected to alter the cellular level of various lipid second messengers such as PA, $IP_3$ and DAG (Kent, *Anal. Rev. Biochem.* 64:315–343, 1995) and hence modulates cytokine induced signaling response in cells. To test this hypothesis, a CDS expression plasmid (pCE2.hCDS), or vector (pCE2) were stably transfected into ECV304 cells (American Type Culture Collection, Rockville, Md.), an endothelial cell line that produces IL-6 and TNF-$\alpha$ upon stimulation with IL-1$\beta$. FIG. 7 shows that the secretion of TNF-$\alpha$ IL-6 in ECV304 cells stably transfected with CDS expression vector increased by >5 fold relative to ECV304 cells stably transfected with control vector after stimulation with 1 ng/ml IL-1$\beta$. However, there was little effect on the basal level of cytokine release, suggesting that over-expression of CDS amplified the cytokine signaling response, as opposed to enhancing the steady-state, basal signal, in these cells.

CDS Polypeptide Synthesis

Polypeptides of the present invention can be synthesized by such commonly used methods as t-BOC or FMOC protection of alpha-amino groups. Both methods involve step-wise syntheses whereby a single amino acid is added at each step starting from the C-terminus of the peptide (Coligan et al., *Current Protocols in Immunology*, Wiley Interscience, Unit 9, 1991). In addition, polypeptides of the present invention can also be synthesized by solid phase synthesis methods (e.g., Merrifield, *J. Am. Chem. Soc.* 85:2149, 1962; and Steward and Young, *Solid Phase Peptide Synthesis*, Freeman, San Francisco pp. 27–62, 1969) using copolyol (styrene-divinylbenzene) containing 0.1–1.0 mM amines/g polymer. On completion of chemical synthesis, the ploypeptides can be deprotected and cleaved from the polymer by treatment with liquid HF 10% anisole for about 15–60 min at 0° C. After evaporation of the reagents, the peptides are extracted from the polymer with 1% acetic acid solution, which is then lyophilized to yield crude material. This can normally be purified by such techniques as gel filtration of Sephadex G-15 using 5% acetic acid as a solvent. Lyophilization of appropriate fractions of the column will yield a homogeneous polypeptide or polypeptide derivatives, which are characterized by such standard techniques as amino acid analysis, thin layer chromatography, high performance liquid chromatography, ultraviolet absorption spectroscopy, molar rotation, solubility and quantitated by solid phase Edman degradation.

CDS Polynucleotides

The invention also provides polynucleotides which encode the CDS polypeptide of the invention. As used herein, "polynucleotide" refers to a polymer of deoxyribonucleotides or ribonucleotides in the form of a separate fragment or as a component of a larger construct. DNA encoding the polypeptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. Preferably, the nucleotide sequence encoding CDS is sequence SEQ ID NO. 1. DNA sequences of the present invention can be obtained by several methods. For example, the DNA can be isolated using hybridization procedures which are known in the art. Such hybridization procedures include, for example, hybridization of probes to genomic or cDNA libraries to detect shared nucleotide sequences, antibody screening of expression libraries to detect common antigenic epitopes or shared structural features and synthesis by the polymerase chain reaction (PCR).

Hybridization procedures are useful for screening recombinant clones by using labeled mixed synthetic oligonucleotides probes, wherein each probe is potentially the complete complement of a specific DNA sequence in a hybridization sample which includes a heterogeneous mixture of denatured double-stranded DNA. For such screening, hybridization is preferably performed on either single-stranded DNA or denatured double-stranded DNA. Hybridization is particularly useful for detection of cDNA clones derived from sources where an extremely low amount of mRNA sequences relating to the polypeptide of interest are present. Using stringent hybridization conditions avoid nonspecific binding, it is possible to allow an autoradiographic visualization of a specific genomic DNA or cDNA clone by the hybridization of the target DNA to a radiolabeled probe, which is its complement (Wallace et al. *Nucl. Acid Res.* 9:879, 1981). Specific DNA sequences encoding CDS can also be obtained by isolation and cloning of double-stranded DNA sequences from the genomic DNA, chemical manufacture of a DNA sequence to provide the necessary codons for the complete polypeptide of interest or portions of the sequence for use in PCR to obtain the complete sequence, and in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of cDNA clones is the most useful. This is especially true when it is desirable to obtain the microbial expression of mammalian polypeptides since the presence of introns in genomic DNA clones can prevent accurate expression.

The synthesis of DNA sequences is sometimes a method that is preferred when the entire sequence of amino acids residues of the desired polypeptide product is known. When the entire sequence of amino acid residues of the desired polypeptide is not known, direct synthesis of DNA sequences is not possible and it is desirable to synthesize cDNA sequences. cDNA sequence isolation can be done, for example, by formation of plasmid- or phage-carrying cDNA libraries which are derived from reverse transcription of mRNA. mRNA is abundant in donor cells that have high levels of genetic expression. In the event of lower levels of expression, PCR techniques can be used to isolate and amplify the cDNA sequence of interest. Using synthesized oligonucleotides corresponding exactly, or with some degeneracy, to known CDS amino acid or nucleotide sequences, one can use PCR to obtain and clone the sequence between the oligonucleotides. The oligonucleotide may represent invariant regions of the CDS sequence and PCR may identify sequences (isoforms) with variations from SEQ ID NO. 1.

A cDNA expression library, such as lambda gt11, can be screened indirectly for the CDS polypeptide, using antibodies specific for CDS. Such antibodies can be either polyclonal or monoclonal, derived from the entire CDS protein or fragments thereof, and used to detect and isolate expressed proteins indicative of the presence of CDS cDNA.

A polynucleotide sequence can be deduced from an amino acid sequence by using the genetic code, however the degeneracy of the code must be taken into account. Polynucleotides of this invention include variant polynucleotide sequences which code for the same amino acids as a result of degeneracy in the genetic code. There are 20 natural amino acids, most of which are specified by more that one codon (a three base sequence). Therefore, as long as the amino acid sequence of CDS results in a functional polypeptide (at least, in the case of the sense polynucleotide strand), all degenerate nucleotide sequences are included in the invention. The polynucleotide sequence for CDS also includes sequences complementary to the polynucleotides encoding CDS (antisense sequences). Antisense nucleic acids are DNA, and RNA molecules that are complementary to at least a portion of a specific mRNA molecule (Weintraub, *Sci. Amer.* 262:40, 1990). The invention embraces all antisense polynucleotides capable of inhibiting the production of CDS polypeptide. In the cell, the antisense nucleic acids hybridize to the corresponding mRNA, forming a double-stranded molecule. The antisense nucleic acids interfere with the translation of mRNA since the cell cannot translate mRNA that is double-stranded. Antisense oligomers of about 15 nucleotides are preferred, since they are easily synthesized and are less likely to cause problems than larger molecules when introduced into the target CDS-producing cell. The use of antisense methods to inhibit translation of genes is known (e.g., Marcus-Sakura, *Anal. Biochem.* 172:289, 1988).

In addition, ribozyme nucleotide sequences for CDS are included in this invention. Ribozymes are hybrid RNA:DNA molecules possessing an ability to specifically cleave other single-stranded RNA in a manner analogous to DNA restriction endonucleases. Through the modification of nucleotide sequences which encode such RNAs, it is possible to engineer molecules that recognize specific nucleotide sequences in an RNA molecule and cleave it (Cech, *J. Amer. Med. Assn.* 260:3030, 1988). An advantage of this approach is that only mRNAs with particular sequences are inactivated because they are sequence-specific.

The CDS DNA sequence may be inserted into an appropriate recombinant expression vector. The term "recombinant expression vector" refers to a plasmid, virus or other vehicle that has been manipulated by insertion or incorporation of the genetic sequences. Such expression vectors contain a promoter sequence which facilitates efficient transcription of the inserted genetic sequence in the host. The expression vector typically contains an origin of replication, a promoter, as well as specific genes which allow phenotypic selection of the transformed cells. Vectors suitable for use in the present invention include, for example, vectors with a bacterial promoter and ribosome binding site for expression in bacteria (Gold, *Meth. Enzymol.* 185:11, 1990), expression vectors with mammalian or viral promoter and enhancer for expression in mammalian cells (Kaufman, *Meth. Enzymol.* 185:487, 1990) and baculovirus-derived vectors for expression in insect cells (Luckow et al., *J. Virol.* 67:4566, 1993). The DNA segment can be present in the vector operably linked to regulatory elements, for example, constitutive or inducible promoters (e.g., T7, metallothionein I, CMV, or polyhedren promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyltransferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoriboseyltransferase (XGPRT, gpt).

In another preferred embodiment, the expression system used is one driven by the baculovirus polyhedrin promoter. The gene encoding the polypeptide can be manipulated by standard techniques in order to facilitate cloning into the baculovirus vector. A preferred baculovirus vector is the pBlueBac vector (Invitrogen, Sorrento, Calif.). The vector carrying the gene for the polypeptide is transfected into *Spodoptera frugiperda* (Sf9) cells by standard protocols, and the cells are cultured and processed to produce the recombinant polypeptide. See Summers et al., *A Manual for Methods of Baculovirus Vectors and Insect Cell Culture Procedures*, Texas Agricultural Experimental Station.

Once the entire coding sequence of the gene for the polypeptides has been determined, the gene can be expressed in any number of different recombinant DNA expression systems to generate large amounts of polypeptide. Included within the present invention are polypeptides having native glycosylation sequences, and deglycosylated or unglycosylated polypeptides prepared by the methods described below. Examples of expression systems known to the skilled practitioner in the art include bacteria such as *E. coli*, yeast such as *Pichia pastoris*, baculovirus, and mammalian expression systems such as in COS or CHO cells.

The gene or gene fragment encoding the desired polypeptide can be inserted into an expression vector by standard subcloning techniques. In a preferred embodiment, an *E. coli* expression vector is used which produces the recombinant protein as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the thiofusion system (Invotrogen, San Diego, Calif.), the FLAG system (IBI, New Haven, Conn.), and the 6xHis system (Qiagen, Chatsworth, Calif.). Some of these systems produce recombinant polypeptides bearing only a small number of additional amino acids, which are unlikely to affect the CDS activity of the recombinant polypeptide. For example, both the FLAG system and the 6xHis system add only short sequences, both of which are known to be poorly antigenic and which do not adversely affect folding of the polypeptide to its native conformation. Other fusion systems produce proteins where it is desirable to excise the fusion partner from the desired protein. In a preferred embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.) or enterokinase (Invotrogen, San Diego, Calif.).

Production of Polypeptides

Polynucleotide sequences encoding the CDS polypeptides of the invention can be expressed in either prokaryotes or eukaryotes after insertion. Hosts can include microbial (bacterial), yeast, insect and mammalian organisms. Methods of expressing eukaryotic or viral DNA sequences in prokaryotes are known in the art. Biologically functional viral and plasmid DNA vectors capable of expression and replication in a host are known in the art. Such vectors are used to incorporate DNA sequences of the invention. DNA sequences encoding the inventive polypeptides can be expressed in vitro by DNA transfer into a suitable host cell using known methods of transfection.

In a preferred embodiment, recombinant proteins are expressed in *E. coli* or in baculovirus expression systems. The complete gene for the polypeptide can be expressed or, alternatively, fragments of the gene encoding antigenic determinants can be produced. In a first preferred embodiment, the gene sequence encoding the polypeptide is analyzed to detect putative transmembrane sequences. Such sequences are typically very hydrophobic and are readily detected by the use of standard sequence analysis software, such as MacDNASIS (Hitachi, San Bruno, Calif.). The presence of transmembrane sequences is often deleterious when a recombinant protein is synthesized in many expression systems, especially *E. coli*, as it leads to the production of insoluble aggregates which are difficult to renature into the native conformation of the polypeptide. Deletion of transmembrane sequences at the ends of the polypeptide typically does not significantly alter the conformation of the remaining polypeptide structure. Moreover, transmembrane sequences, being by definition embedded within a membrane, are inaccessible as antigenic determinants to a host immune system. Antibodies to these sequences will not, therefore, provide immunity to the host and, hence, little is lost in terms of immunity by omitting such sequences from the recombinant polypeptides of the invention. Deletion of transmembrane-encoding sequences from the genes used for expression can be achieved by standard techniques. For example, fortuitously-placed restriction enzyme sites can be used to excise the desired gene fragment, or the PCR can be used to amplify only the desired part of the gene.

Transformation of a host cell with recombinant DNA may be carried out by conventional techniques. When the host is prokaryotic, such as *E. coli*, competent cells which are capable of DNA uptake can be prepared from cells harvested after exponential growth phases and subsequently treated by a $CaCl_2$ method using standard procedures. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures, such as microinjection, electroporation, insertion of a plasmid encased in a liposome, or virus vectors may be used. Eukaryotic cells can also be cotransformed with DNA sequences encoding the CDS polypeptides of the invention, and a second foreign DNA molecule encoding a selectable phenotype, such as the herpes simplex thymidine kinase gene. Another method uses a eukaryotic viral vector, such as simian virus 40 (SV40) or bovine papilloma virus to transiently infect or transform eukaryotic cells and express the CDS polypeptide.

Expression vectors that are suitable for production of CDS polypeptides typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; or enhancer elements and (3) DNA elements that control the processing of transcripts, such as a transcription termination/polyadenylation sequence. CDS polypeptides of the present invention preferably are expressed in eukaryotic cells, such as mammalian, insect and yeast cells. Mammalian cells are especially preferred eukaryotic hosts because mammalian cells provide suitable post-translational modifications such as glycosylation. Examples of mammalian host cells include Chinese hamster ovary cells (CHO-K1; ATCC CCL61), NCI-H460 cells, rat pituitary cells ($GH_1$; ATCC CCL82), HeLa S3 cells (ATCC CCL2.2), rat hepatoma cells (H-4-II-E; ATCC CRL1548) SV40-transformed monkey kidney cells (COS-1; ATCC CRL 1650) and murine embryonic cells (NIH-3T3; ATCC CRL 1658). For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273,1982); the TK promoter of Herpes virus (McKnight, *Cell* 31: 355, 1982); the SV40 early promoter (Benoist et al., *Nature* 290:304, 1981); the Rous sarcoma virus promoter (Gorman et al., *Proc. Nat'l. Acad. Sci. USA* 79:6777, 1982); and the cytomegalovirus promoter (Foecking et al., *Gene* 45:101, 1980). Alternatively, a prokaryotic promoter, such as the bacteriophage T3 RNA polymerase promoter, can be used to control fusion gene expression if the prokaryotic promoter is regulated by a eukaryotic promoter (Zhou et al., *Mol. Cell. Biol.* 10:4529, 1990; and Kaufman et al., *Nucl. Acids Res.* 19:4485, 1991).

An expression vector can be introduced into host cells using a variety of techniques including calcium phosphate transfection, liposome-mediated transfection, electroporation, and the like. Preferably, transfected cells are selected and propagated wherein the expression vector is stably integrated in the host cell genome to produce stable transfectants. Techniques for introducing vectors into eukaryotic cells and techniques for selecting stable transfectants using a dominant selectable marker are described, for example, by Ausubel and Murray (ed.), *Gene Transfer and Expression Protocols* (Humana Press 1991). Examples of mammalian host cells include COS, BHK, 293 and CHO cells.

Purification of Recombinant Polypeptides.

The polypeptide expressed in recombinant DNA expression systems can be obtained in large amounts and tested for biological activity. The recombinant bacterial cells, for example *E. coli*, are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed. If the recombinant polypeptide is expressed in the inclusion, these can be washed in any of several solutions to remove some of the contaminating host proteins, then solubilized in solutions containing high concentrations of urea (e.g., 8 M) or chaotropic agents such as guanidine hydrochloride in the presence of reducing agents such as β-mercaptoethanol or DTT (dithiothreitol). At this stage it may be advantageous to incubate the polypeptide for several hours under conditions suitable for the polypeptide to undergo a refolding process into a conformation which more closely resembles that of the native polypeptide. Such conditions generally include low polypeptide (concentrations less than 500 mg/ml), low levels of reducing agent, concentrations of urea less than 2 M and often the presence of reagents such as a mixture of reduced and oxidized glutathione which facilitate the interchange of disulphide bonds within the protein molecule. The refolding process can be monitored, for example, by SDS-PAGE or with antibodies which are specific for the native molecule. Following refolding, the polypeptide can then be purified further and separated from the refolding mixture by chromatography on any of several supports including ion exchange resins, gel permeation resins or on a variety of affinity columns.

Isolation and purification of host cell expressed polypeptide, or fragments thereof may be carried out by conventional means including, but not limited to, preparative chromatography and immunological separations involving monoclonal or polyclonal antibodies.

These polypeptides may be produced in a variety of ways, including via recombinant DNA techniques, to enable large scale production of pure, active CDS useful for screening compounds for trilineage hematopoietic and anti-inflammatory therapeutic applications, and developing antibodies for therapeutic, diagnostic and research use.

Screening Assays Using CDS Polypeptides

The CDS polypeptide of the present invention is useful in a screening methodology for identifying compounds or compositions which affect cellular signaling of an inflammatory response. This method comprises incubating the CDS polypeptides or a cell transfected with cDNA encoding CDS under conditions sufficient to allow the components to interact, and then measuring the effect of the compound or composition on CDS activity. The observed effect on CDS may be either inhibitory or stimulatory.

Peptide Sequencing of Polypeptides

Substitutional variants typically contain the exchange of one amino acid for another at one or more sites within the protein, and are designed to modulate one or more properties of the polypeptides such as stability against proteolytic cleavage. Substitutions preferably are conservative, that is, one amino acid is replaced with one of similar shape and charge. Conservative substitutions are well known in the art and include, for example, the changes of: alanine to serine; arginine to lysine; asparigine to glutamine or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Insertional variants contain fusion proteins such as those used to allow rapid purification of the polypeptide and also can include hybrid polypeptides containing sequences from other proteins and polypeptides which are homologues of the inventive polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptides. These typically are smaller insertions than the fusion proteins described above and are introduced, for example, to disrupt a protease cleavage site.

Anti-CDS Antibodies

Antibodies to human CDS protein can be obtained using the product of an CDS expression vector or synthetic peptides derived from the CDS coding sequence coupled to a carrier (Pasnett et al., *J. Biol. Chem.* 263:1728, 1988) as an antigen. The preparation of polyclonal antibodies is well-known to those of skill in the art. See, for example, Green et al., "Production of Polyclonal Antisera," in *Immunochemical Protocols* (Manson, ed.), pages 1–5 (Humana Press 1992). Alternatively, a CDS antibody of the present invention may be derived as a rodent monoclonal antibody (MAb). Rodent monoclonal antibodies to specific antigens may be obtained by methods known to those skilled in the art. See, for example, Kohler and Milstein, *Nature* 256:495, 1975, and Coligan et al. (eds.), *Current Protocols in Immunology*, 1:2.5.1–2.6.7 (John Wiley & Sons 1991). Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1–2.7.12 and pages 2.9.1–2.9.3. Also, see Baines et al., "Purification of Immunoglobulin G (IgG)," in *Methods in Molecular Biology*, 10:79–104 Humana Press, Inc. 1992. A CDS antibody of the present invention may also be derived from a subhuman primate. General techniques for raising therapeutically useful antibodies in baboons may be found, for example, in Goldenberg et al., international patent publication No. WO 91/11465 (1991), and in Losman et al., *Int. J. Cancer* 46:310, 1990.

Alternatively, a therapeutically useful CDS antibody may be derived from a "humanized" monoclonal antibody. Humanized monoclonal antibodies are produced by transferring mouse complementarity determining regions from heavy and light chain variable regions of the mouse antibody into a human antibody variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l. Acad. Sci. USA* 86:3833, 1989. Techniques for producing humanized MAbs are described, for example, by Jones et al., *Nature* 321:522, 1986; Riechmann et al., Nature 332:323, 1988; Verhoeyen et al., *Science* 239:1534, 1988; Carter et al., *Proc. Nat'l Acad. Sci. USA* 89:4285, 1992; Sandhu, *Crit. Rev. Biotech.* 12:437, 1992; and Singer et al., *J. Immun.* 150:2844, 1993.

As an alternative, a CDS antibody of the present invention may be derived from human antibody fragments isolated from a combinatorial immunoglobulin library. See, for example, Barbas et al., METHODS: *A Companion to Methods in Enzymology* 2:119 1991, and Winter et al., *Ann. Rev. Immunol.* 12:433, 1994. Cloning and expression vectors that are useful for producing a human immunoglobulin phage library can be obtained, for example, from STRATAGENE Cloning Systems (La Jolla, Calif.). In addition, a CDS antibody of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immun.* 6:579, 1994.

We claim:

1. A nucleic acid sequence coding for expression of CDP-diacylglycerol synthase, selected from the group consisting of:

(a) a DNA sequence set forth in SEQ ID NO. 1 and enzymatically active fragments thereof;

(b) a cDNA sequence which, due to the degeneracy of the genetic code, encodes a polypeptide of SEQ ID NO. 2 and enzymatically active fragments thereof; and (c) a cDNA sequence capable of hybridizing to the cDNA of (a) or (b) under high stringency conditions and which encodes a polypeptide having CDP-diacylglycerol synthase activity.

* * * * *

SEQUENCE LISTING (1) GENERAL INFORMATION:

(iii) NUMBER OF SEQUENCES:13

(2) INFORMATION FOR SEQ ID NO:1:

(i) SEQUENCE CHARACTERISTICS:
      (A) LENGTH:2051
      (B) TYPE: nucleic acid
      (C) STRANDEDNESS: double stranded
      (D) TOPOLOGY: linear (ii) MOLECULE TYPE: cDNA to mRNA (iii) HYPOTHETICAL: no (iv) ANTI-SENSE: no (v) FRAGMENT TYPE:

(vi) ORIGINAL SOURCE:
      (A) ORGANISM: homo sapien
      (B) STRAIN:
      (C) INDIVIDUAL ISOLATE:
      (D) DEVELOPMENTAL STAGE:
      (E) HAPLOTYPE:
      (F) TISSUE TYPE:
      (G) CELL TYPE:
      (H) CELL LINE:
      (I) ORGANELLE:

(ix) FEATURE:
      (A) NAME/KEY: CDS (xi) SEQUENCE DESCRIPTION: SEQ ID NO:1:

```
TCTATGGTGG GGCCGCGTTA GTGGCTGCGG CTCCGCGGGA CTCCAGGGCG              50

CGGCTGCGAG GTGGCGGGGC GCCCCGCCTG CAGAACCCTG CTTGCAGCTC             100

AGGTTTCGGG GTGCTTGAGG AGGCCGCCAC GGCAGCGCGG GAGCGGAAG              149

ATG TTG GAG CTG AGG CAC CGG GGA AGC TGC CCC GGC CCC AGG GAA       194
Met Leu Glu Leu Arg His Arg Gly Ser Cys Pro Gly Pro Arg Glu
 1               5                  10                  15

GCG GTG TCG CCG CCA CAC CGC GAG GGA GAG GCG GCC GGC GGC GAC       239
Ala Val Ser Pro Pro His Arg Glu Gly Glu Ala Ala Gly Gly Asp
                20                  25                  30

CAC GAA ACC GAG AGC ACC AGC GAC AAA GAA ACA GAT ATT GAT GAC       284
His Glu Thr Glu Ser Thr Ser Asp Lys Glu Thr Asp Ile Asp Asp
                35                  40                  45

AGA TAT GGA GAT TTG GAT TCC AGA ACA GAT TCT GAT ATT CCG GAA       329
Arg Tyr Gly Asp Leu Asp Ser Arg Thr Asp Ser Asp Ile Pro Glu
                50                  55                  60

ATT CCA CCA TCC TCA GAT AGA ACC CCT GAG ATT CTC AAA AAA GCT       374
Ile Pro Pro Ser Ser Asp Arg Thr Pro Glu Ile Leu Lys Lys Ala
                65                  70                  75

CTA TCT GGT TTA TCT TCA AGG TGG AAA AAC TGG TGG ATA CGT GGA       419
Leu Ser Gly Leu Ser Ser Arg Trp Lys Asn Trp Trp Ile Arg Gly
                80                  85                  90

ATT CTC ACT CTA ACT ATG ATC TCG TTG TTT TTC CTG ATC ATC TAT       464
Ile Leu Thr Leu Thr Met Ile Ser Leu Phe Phe Leu Ile Ile Tyr
                95                  100                 105

ATG GGA TCC TTC ATG CTG ATG CTT CTT GTT CTG GGC ATC CAA GTG       509
Met Gly Ser Phe Met Leu Met Leu Leu Val Leu Gly Ile Gln Val
                110                 115                 120
```

```
AAA TGC TTC CAT GAA ATT ATC ACT ATA GGT TAT AGA GTC TAT CAT      554
Lys Cys Phe His Glu Ile Ile Thr Ile Gly Tyr Arg Val Tyr His
            125                 130                 135

TCT TAT GAT CTA CCA TGG TTT AGA ACA CTA AGT TGG TAC TTT CTA      599
Ser Tyr Asp Leu Pro Trp Phe Arg Thr Leu Ser Trp Tyr Phe Leu
            140                 145                 150

TTG TGT GTA AAC TAC TTT TTC TAT GGA GAG ACT GTA GCT GAT TAT      644
Leu Cys Val Asn Tyr Phe Phe Tyr Gly Glu Thr Val Ala Asp Tyr
            155                 160                 165

TTT GCT ACA TTT GTT CAA AGA GAA GAA CAA CTT CAG TTC CTC ATT      689
Phe Ala Thr Phe Val Gln Arg Glu Glu Gln Leu Gln Phe Leu Ile
            170                 175                 180

CGC TAC CAT AGA TTT ATA TCA TTT GCC CTC TAT CTG GCA GGT TTC      734
Arg Tyr His Arg Phe Ile Ser Phe Ala Leu Tyr Leu Ala Gly Phe
            185                 190                 195

TGC ATG TTT GTA CTG AGT TTG GTG AAG GAA CAT TAT CGT CTG CAG      779
Cys Met Phe Val Leu Ser Leu Val Lys Glu His Tyr Arg Leu Gln
            200                 205                 210

TTT TAT ATG TTC GCA TGG ACT CAT GTC ACT TTA CTG ATA ACT GTC      824
Phe Tyr Met Phe Ala Trp Thr His Val Thr Leu Leu Ile Thr Val
            215                 220                 225

ACT CAG TCA CAC CTT GTC ATC CAA AAT CTG TTT GAA GGC ATG ATA      869
Thr Gln Ser His Leu Val Ile Gln Asn Leu Phe Glu Gly Met Ile
            230                 235                 240

TGG TTC CTT GTT CCA ATA TCA AGT GTT ATC TGC AAT GAC ATA ACT      914
Trp Phe Leu Val Pro Ile Ser Ser Val Ile Cys Asn Asp Ile Thr
            245                 250                 255

GCT TAC CTT TTT GGA TTT TTT TTT GGG AGA ACT CCA TTA ATT AAG      959
Ala Tyr Leu Phe Gly Phe Phe Phe Gly Arg Thr Pro Leu Ile Lys
            260                 265                 270

TTG TCT CCT AAA AAG ACT TGG GAA GGA TTC ATT GGT GGT TTC TTT     1004
Leu Ser Pro Lys Lys Thr Trp Glu Gly Phe Ile Gly Gly Phe Phe
            275                 280                 285

TCC ACA GTT GTG TTT GGA TTC ATT GCT GCC TAT GTG TTA TCC AAA     1049
Ser Thr Val Val Phe Gly Phe Ile Ala Ala Tyr Val Leu Ser Lys
            290                 295                 300

TAC CAG TAC TTT GTC TGC CCA GTG GAA TAC CGA AGT GAT GTA AAC     1094
Tyr Gln Tyr Phe Val Cys Pro Val Glu Tyr Arg Ser Asp Val Asn
            305                 310                 315

TCC TTC GTG ACA GAA TGT GAG CCC TCA GAA CTT TTC CAG CTT CAG     1139
Ser Phe Val Thr Glu Cys Glu Pro Ser Glu Leu Phe Gln Leu Gln
            320                 325                 330

ACT TAC TCA CTT CCA CCC TTT CTA AAG GCA GTC TTG AGA CAG GAA     1184
Thr Tyr Ser Leu Pro Pro Phe Leu Lys Ala Val Leu Arg Gln Glu
            335                 340                 345

AGA GTG AGC TTG TAC CCT TTC CAG ATC CAC AGC ATT GCA CTG TCA     1229
Arg Val Ser Leu Tyr Pro Phe Gln Ile His Ser Ile Ala Leu Ser
            350                 355                 360

ACC TTT GCA TCT TTA ATT GGC CCA TTT GGA GGC TTC TTT GCT AGT     1274
Thr Phe Ala Ser Leu Ile Gly Pro Phe Gly Gly Phe Phe Ala Ser
            365                 370                 375

GGA TTC AAA AGA GCC TTC AAA ATC AAG GAT TTT GCA AAT ACC ATT     1319
Gly Phe Lys Arg Ala Phe Lys Ile Lys Asp Phe Ala Asn Thr Ile
            380                 385                 390

CCT GGA CAT GGT GGG ATA ATG GAC AGA TTT GAT TGT CAG TAT TTG     1364
Pro Gly His Gly Gly Ile Met Asp Arg Phe Asp Cys Gln Tyr Leu
            395                 400                 405

ATG GCA ACT TTG GTA CAT GGN TAC ATC ACA AGT TTT ATA AGG GGC     1409
Met Ala Thr Leu Val His Gly Tyr Ile Thr Ser Phe Ile Arg Gly
            410                 415                 420
```

```
CCA AAT CCC AGC AAA GTG CTA CAG CAG TTG TTG GTG CTT CAA CCT         1454
Pro Asn Pro Ser Lys Val Leu Gln Gln Leu Leu Val Leu Gln Pro
            425                 430                 435

GAA CAG CAG TTA AAT ATA TAT AAA ACC CTG AAG ACT CAT CTC ATT         1499
Glu Gln Gln Leu Asn Ile Tyr Lys Thr Leu Lys Thr His Leu Ile
            440                 445                 450

GAG AAA GGA ATC CTA CAA CCC ACC TTG AAG GTA TAA                     1535
Glu Lys Gly Ile Leu Gln Pro Thr Leu Lys Val
            455                 460

CTGGATCCAG AGAGGGAAGG ACTGACAAGA AGGAATTATT CAGAAAAACA              1585

CTGACAGATG TTTTATAAAT TGTACAGAAA AATAGTTAAA AATGCAATAG              1635

GTTGAAGTTT TGGAGATATG TTTCTCTCTG AAATTACTGT GAATATTTAA              1685

CAAACACTTA CTTGATCTAT GTTATGAAAT AAGTAGCAAA TTGCCAGCAA              1735

AATGTCTTGT ACCTTTTCTA AAGTGTATTT TCTGATGTGA ACTTCCTTCC              1785

CCTTACTTGC TAGGTTTCAT AATTTAAAAG ACTGGTATTT AAAAGAGTCA              1835

AACACTATAA AATGAGTAAG TTGACGATGT TTTAAGATTG CACCTGGCAG              1885

TGTGCCTTTT TGCACAAATA TTTACTTTTG CACTTGGAGC TGCTTTTAAT              1935

TTTAGCAAAA TGTTTTATGC AAGGCACAAT AGGAAGTCAG TTCTCCTGCA              1985

CTTCCTCCTC ATGTAGTCTG GAGTACTTTC TAAAGGGCTT AGTTGGATTT              2035

AAAAAAAAAA AAAAAA                                                    2051

(2) INFORMATION FOR SEQ ID NO:2:

(i) SEQUENCE CHARACTERISTICS:
        (A) LENGTH: 461
        (B) TYPE: amino acid
        (C) STRANDEDNESS: single
        (D) TOPOLOGY: linear (ii) MOLECULE TYPE: polypeptide (iii) HYPOTHETICAL: no (iv) ANTI-SENSE: NO (v) FRAGMENT TYPE:

(vi) ORIGINAL SOURCE:
        (A) ORGANISM: homo sapien
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(ix) FEATURE:
        (A) NAME/KEY: CDS
        (B) LOCATION:
        (C) IDENTIFICATION METHOD:
        (D) OTHER INFORMATION:

(xi) SEQUENCE DESCRIPTION: SEQ ID NO:2:

Met Leu Glu Leu Arg His Arg Gly Ser Cys Pro Gly Pro Arg Glu
 1               5                  10                  15

Ala Val Ser Pro Pro His Arg Glu Gly Glu Ala Ala Gly Gly Asp
                20                  25                  30

His Glu Thr Glu Ser Thr Ser Asp Lys Glu Thr Asp Ile Asp Asp
                35                  40                  45
```

```
Arg Tyr Gly Asp Leu Asp Ser Arg Thr Asp Ser Asp Ile Pro Glu
                50                  55                  60

Ile Pro Pro Ser Ser Asp Arg Thr Pro Glu Ile Leu Lys Lys Ala
                65                  70                  75

Leu Ser Gly Leu Ser Ser Arg Trp Lys Asn Trp Trp Ile Arg Gly
                80                  85                  90

Ile Leu Thr Leu Thr Met Ile Ser Leu Phe Phe Leu Ile Ile Tyr
                95                 100                 105

Met Gly Ser Phe Met Leu Met Leu Leu Val Leu Gly Ile Gln Val
               110                 115                 120

Lys Cys Phe His Glu Ile Ile Thr Ile Gly Tyr Arg Val Tyr His
               125                 130                 135

Ser Tyr Asp Leu Pro Trp Phe Arg Thr Leu Ser Trp Tyr Phe Leu
               140                 145                 150

Leu Cys Val Asn Tyr Phe Phe Tyr Gly Glu Thr Val Ala Asp Tyr
               155                 160                 165

Phe Ala Thr Phe Val Gln Arg Glu Gln Leu Gln Phe Leu Ile
               170                 175                 180

Arg Tyr His Arg Phe Ile Ser Phe Ala Leu Tyr Leu Ala Gly Phe
               185                 190                 195

Cys Met Phe Val Leu Ser Leu Val Lys Glu His Tyr Arg Leu Gln
               200                 205                 210

Phe Tyr Met Phe Ala Trp Thr His Val Thr Leu Leu Ile Thr Val
               215                 220                 225

Thr Gln Ser His Leu Val Ile Gln Asn Leu Phe Glu Gly Met Ile
               230                 235                 240

Trp Phe Leu Val Pro Ile Ser Ser Val Ile Cys Asn Asp Ile Thr
               245                 250                 255

Ala Tyr Leu Phe Gly Phe Phe Gly Arg Thr Pro Leu Ile Lys
               260                 265                 270

Leu Ser Pro Lys Lys Thr Trp Glu Gly Phe Ile Gly Gly Phe Phe
               275                 280                 285

Ser Thr Val Val Phe Gly Phe Ile Ala Ala Tyr Val Leu Ser Lys
               290                 295                 300

Tyr Gln Tyr Phe Val Cys Pro Val Glu Tyr Arg Ser Asp Val Asn
               305                 310                 315

Ser Phe Val Thr Glu Cys Glu Pro Ser Glu Leu Phe Gln Leu Gln
               320                 325                 330

Thr Tyr Ser Leu Pro Pro Phe Leu Lys Ala Val Leu Arg Gln Glu
               335                 340                 345

Arg Val Ser Leu Tyr Pro Phe Gln Ile His Ser Ile Ala Leu Ser
               350                 355                 360

Thr Phe Ala Ser Leu Ile Gly Pro Phe Gly Phe Ala Ser
               365                 370                 375

Gly Phe Lys Arg Ala Phe Lys Ile Lys Asp Phe Ala Asn Thr Ile
               380                 385                 390

Pro Gly His Gly Gly Ile Met Asp Arg Phe Asp Cys Gln Tyr Leu
               395                 400                 405

Met Ala Thr Leu Val His Gly Tyr Ile Thr Ser Phe Ile Arg Gly
               410                 415                 420

Pro Asn Pro Ser Lys Val Leu Gln Gln Leu Leu Val Leu Gln Pro
               425                 430                 435

Glu Gln Gln Leu Asn Ile Tyr Lys Thr Leu Lys Thr His Leu Ile
               440                 445                 450
```

```
Glu Lys Gly Ile Leu Gln Pro Thr Leu Lys Val
            455                 460

(2) INFORMATION FOR SEQ ID NO:3:

(i) SEQUENCE CHARACTERISTICS:
        (A) LENGTH:38
        (B) TYPE: amino acid
        (C) STRANDEDNESS: single
        (D) TOPOLOGY: linear (ii) MOLECULE TYPE: polypeptide (iii) HYPOTHETICAL: no (iv) ANTI-SENSE: NO (v) FRAGMENT TYPE:

(vi) ORIGINAL SOURCE:
        (A) ORGANISM: Drosophila
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(ix) FEATURE:
        (A) NAME/KEY: CDS fragment
        (B) LOCATION:371-408
        (C) IDENTIFICATION METHOD:

(xi) SEQUENCE DESCRIPTION: SEQ ID NO:3:

Lys Arg Ala Phe Lys Ile Lys Asp Phe Gly Asp Met Ile Pro Gly
 1               5                  10                  15

His Gly Gly Ile Met Asp Arg Phe Asp Cys Gln Phe Leu Met Ala
                20                  25                  30

Thr Phe Val Asn Val Tyr Ile Ser
                35

(2) INFORMATION FOR SEQ ID NO:4:

(i) SEQUENCE CHARACTERISTICS:
        (A) LENGTH:38
        (B) TYPE: amino acid
        (C) STRANDEDNESS: single
        (D) TOPOLOGY: linear (ii) MOLECULE TYPE: polypeptide (iii) HYPOTHETICAL: no (iv) ANTI-SENSE: no (v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(ix) FEATURE:
        (A) NAME/KEY: IMAGE clone #135630
        (B) LOCATION: 11-124
        (C) IDENTIFICATION METHOD:
```

(D) OTHER INFORMATION:

(xi) SEQUENCE DESCRIPTION: SEQ ID NO:4:

Lys Arg Ala Phe Lys Ile Lys Asp Phe Ala Asn Thr Ile Pro Gly
 1               5                  10                  15

His Gly Gly Ile Met Asp Arg Phe Asp Cys Gln Tyr Leu Met Ala
                 20                  25                  30

Thr Phe Val His Val Tyr Ile Thr
                35

(2) INFORMATION FOR SEQ ID NO:5:

(i) SEQUENCE CHARACTERISTICS:
        (A) LENGTH:27
        (B) TYPE: nucleotide
        (C) STRANDEDNESS: single
        (D) TOPOLOGY: linear (ii) MOLECULE TYPE: oligonucleotide fragment (iii) HYPOTHETICAL: no (iv) ANTI-SENSE: no (v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(ix) FEATURE:
        (A) NAME/KEY: o.h.cds.1R
        (B) LOCATION:
        (C) IDENTIFICATION METHOD:
        (D) OTHER INFORMATION:

(xi) SEQUENCE DESCRIPTION: SEQ ID NO:5:

CCCACCATGG CCAGGAATGG TATTTGC                                              27

(2) INFORMATION FOR SEQ ID NO:6:

(i) SEQUENCE CHARACTERISTICS:
        (A) LENGTH:25
        (B) TYPE: nucleotide
        (C) STRANDEDNESS: single
        (D) TOPOLOGY: linear (ii) MOLECULE TYPE: oligonucleotide (iii) HYPOTHETICAL: no (iv) ANTI-SENSE: no (v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(ix) FEATURE:

(A) NAME/KEY: o.h.cds.1
            (B) LOCATION:
            (C) IDENTIFICATION METHOD:
            (D) OTHER INFORMATION:

(xi) SEQUENCE DESCRIPTION: SEQ ID NO:6:

AGTGATGTGA ATTCCTTCGT GACAG                                              25

(2) INFORMATION FOR SEQ ID NO:7:

(i) SEQUENCE CHARACTERISTICS:
           (A) LENGTH:29
           (B) TYPE: nucleic acid
           (C) STRANDEDNESS: single stranded
           (D) TOPOLOGY: linear (ii) MOLECULE TYPE: oligonucleotide (iii) HYPOTHETICAL: no (iv) ANTI-SENSE: no (v) FRAGMENT TYPE:

(vi) ORIGINAL SOURCE:
           (A) ORGANISM:
           (B) STRAIN:
           (C) INDIVIDUAL ISOLATE:
           (D) DEVELOPMENTAL STAGE:
           (E) HAPLOTYPE:
           (F) TISSUE TYPE:
           (G) CELL TYPE:
           (H) CELL LINE:
           (I) ORGANELLE:

(ix) FEATURE:
           (A) NAME/KEY:

(xi) SEQUENCE DESCRIPTION: SEQ ID NO:7:

GGCTCTAGAT ATTAATAGTA ATCAATTAC                                          29

(2) INFORMATION FOR SEQ ID NO:8:

(i) SEQUENCE CHARACTERISTICS:
           (A) LENGTH:26
           (B) TYPE: nucleotide
           (C) STRANDEDNESS: single
           (D) TOPOLOGY: linear (ii) MOLECULE TYPE: oligonucleotide (iii) HYPOTHETICAL: no (iv) ANTI-SENSE: NO (v) FRAGMENT TYPE:

(vi) ORIGINAL SOURCE:
           (A) ORGANISM:
           (B) STRAIN:
           (C) INDIVIDUAL ISOLATE:
           (D) DEVELOPMENTAL STAGE:
           (E) HAPLOTYPE:
           (F) TISSUE TYPE:
           (G) CELL TYPE:
           (H) CELL LINE:
           (I) ORGANELLE:

(ix) FEATURE:
           (A) NAME/KEY:
           (B) LOCATION:
           (C) IDENTIFICATION METHOD:
           (D) OTHER INFORMATION:

(xi) SEQUENCE DESCRIPTION: SEQ ID NO:8:

CCTCACGCAT GCACCATGGT AATAGC									26

(2) INFORMATION FOR SEQ ID NO:9:

(i) SEQUENCE CHARACTERISTICS:
        (A) LENGTH:24
        (B) TYPE: nucleotide
        (C) STRANDEDNESS: single
        (D) TOPOLOGY: linear (ii) MOLECULE TYPE: oligonucleotide (iii) HYPOTHETICAL: no (iv) ANTI-SENSE: NO (v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(ix) FEATURE:
        (A) NAME/KEY:
        (B) LOCATION:
        (C) IDENTIFICATION METHOD:

(xi) SEQUENCE DESCRIPTION: SEQ ID NO:9:

GGTGCATGCG TGAGGCTCCG GTGC									24

(2) INFORMATION FOR SEQ ID NO:10:

(i) SEQUENCE CHARACTERISTICS:
        (A) LENGTH:28
        (B) TYPE: nucleotide
        (C) STRANDEDNESS: single
        (D) TOPOLOGY: linear (ii) MOLECULE TYPE: oligonucleotide (iii) HYPOTHETICAL: no (iv) ANTI-SENSE: no (v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO:10:

GTAGTTTTCA CGGTACCTGA AATGGAAG									28

(2) INFORMATION FOR SEQ ID NO:11:

(i) SEQUENCE CHARACTERISTICS:
    (A) LENGTH: 446
    (B) TYPE: amino acid
    (C) STRANDEDNESS: single
    (D) TOPOLOGY: linear (ii) MOLECULE TYPE: peptide (iii) HYPOTHETICAL: no (iv) ANTI-SENSE: no (v) FRAGMENT TYPE:

(vi) ORIGINAL SOURCE:
    (A) ORGANISM: Drosophila
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(ix) FEATURE:
    (A) NAME/KEY: CDP-diacylglycerol synthase (CDS)
    (B) LOCATION:
    (C) IDENTIFICATION METHOD:
    (D) OTHER INFORMATION:

(xi) SEQUENCE DESCRIPTION: SEQ ID NO:11:

```
Met Ala Glu Val Arg Arg Lys Gly Glu Asp Glu Pro Leu Glu
                  5                  10                  15

Asp Thr Ala Ile Ser Gly Ser Asp Ala Ala Asn Lys Arg Asn Ser
                 20                  25                  30

Ala Ala Asp Ser Ser Asp His Val Asp Ser Glu Glu Glu Lys Ile
                 35                  40                  45

Pro Glu Glu Lys Phe Val Asp Glu Leu Ala Lys Asn Leu Pro Gln
                 50                  55                  60

Gly Thr Asp Lys Thr Pro Glu Ile Leu Asp Ser Ala Leu Lys Asp
                 65                  70                  75

Leu Pro Asp Arg Trp Lys Asn Trp Val Ile Arg Gly Ile Phe Thr
                 80                  85                  90

Trp Ile Met Ile Cys Gly Phe Ala Leu Ile Ile Tyr Gly Gly Pro
                 95                 100                 105

Leu Ala Leu Met Ile Thr Thr Leu Leu Val Gln Val Lys Cys Phe
                110                 115                 120

Gln Glu Ile Ile Ser Ile Gly Tyr Gln Val Tyr Arg Ile His Gly
                125                 130                 135

Leu Pro Trp Phe Arg Ser Leu Ser Trp Tyr Phe Leu Leu Thr Ser
                140                 145                 150

Asn Tyr Phe Phe Tyr Gly Glu Asn Leu Val Asp Tyr Phe Gly Val
                155                 160                 165

Val Ile Asn Arg Val Glu Tyr Leu Lys Phe Leu Val Thr Tyr His
                170                 175                 180

Arg Phe Leu Ser Phe Ala Leu Tyr Ile Ile Gly Phe Val Trp Phe
                185                 190                 195

Val Leu Ser Leu Val Lys Lys Tyr Tyr Ile Lys Gln Phe Ser Leu
                200                 205                 210

Phe Ala Trp Thr His Val Ser Leu Leu Ile Val Val Thr Gln Ser
                215                 220                 225

Tyr Leu Ile Ile Gln Asn Ile Phe Glu Gly Leu Ile Trp Phe Ile
                230                 235                 240
```

```
Val Pro Val Ser Met Ile Val Cys Asn Asp Val Met Ala Tyr Val
                245                 250                 255

Phe Gly Phe Phe Phe Gly Arg Thr Pro Leu Ile Lys Leu Ser Pro
            260                 265                 270

Lys Lys Thr Trp Glu Gly Phe Ile Gly Gly Phe Ala Thr Val
        275                 280                 285

Leu Phe Gly Ile Leu Phe Ser Tyr Val Leu Cys Asn Tyr Gln Tyr
                290                 295                 300

Phe Ile Cys Pro Ile Gln Tyr Ser Glu Glu Gln Gly Arg Met Thr
                305                 310                 315

Met Ser Cys Val Pro Ser Tyr Leu Phe Thr Pro Gln Glu Tyr Ser
                320                 325                 330

Leu Lys Leu Phe Gly Ile Gly Lys Thr Leu Asn Leu Tyr Pro Phe
                335                 340                 345

Ile Trp His Ser Ile Ser Leu Ser Leu Phe Ser Ser Ile Ile Gly
                350                 355                 360

Pro Phe Gly Gly Phe Phe Ala Ser Gly Phe Lys Arg Ala Phe Lys
                365                 370                 375

Ile Lys Asp Phe Gly Asp Met Ile Pro Gly His Gly Gly Ile Met
                380                 385                 390

Asp Arg Phe Asp Cys Gln Phe Leu Met Ala Thr Phe Val Asn Val
                395                 400                 405

Tyr Ile Ser Phe Ile Arg Thr Pro Ser Pro Ala Lys Leu Leu Thr
                410                 415                 420

Gln Ile Tyr Asn Leu Lys Pro Asp Gln Gln Tyr Gln Ile Tyr Gln
                425                 430                 435

Ser Leu Lys Asp Asn Leu Gly His Met Leu Thr
                440                 445

(2) INFORMATION FOR SEQ ID NO:12:

(i) SEQUENCE CHARACTERISTICS:
        (A) LENGTH: 1259
        (B) TYPE: nucleic acid
        (C) STRANDEDNESS: double stranded
        (D) TOPOLOGY: linear (ii) MOLECULE TYPE: cDNA (iii) HYPOTHETICAL: no (iv) ANTI-SENSE: no (v) FRAGMENT TYPE:

(vi) ORIGINAL SOURCE:
        (A) ORGANISM: E. coli
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(ix) FEATURE:
        (A) NAME/KEY: CDP-diglyceride synthetase
        (B) LOCATION:
        (C) IDENTIFICATION METHOD:
        (D) OTHER INFORMATION:

(xi) SEQUENCE DESCRIPTION: SEQ ID NO:12:

GCGTTAAATG CCTTTGCTAA TCGAGAGCGT CGTTTCGGCG GCACCGAGCC CGGTGATGAA        60
```

```
ACAGCCTGAT GGGGGTCGCT TTTGCTGAAG TATCGCCTGA TATCTGCTTT TGTGTTAATA      120

CCCGTCGTCA TCGCGGCGTT GTTTCTGTTG CCGCCGGTGG GGTTCGCCAT TGTAACGCTG      180

GTGGTCTGC ATG CTG GCA GCG TGG GAA TGG GGA CAG CTT AGC GGT TTT          228
          Met Leu Ala Ala Trp Glu Trp Gly Gln Leu Ser Gly Phe
                            5                   10

ACC ACT CGT TCG CAG CGA GTA TGG TTG GCG GTG TTA TGC GGG TTA            273
Thr Thr Arg Ser Gln Arg Val Trp Leu Ala Val Leu Cys Gly Leu
        15                  20                  25

TTG TTG GCG CTG ATG CTT TTT CTG TTG CCG GAA TAT CAC CGA AAT            318
Leu Leu Ala Leu Met Leu Phe Leu Leu Pro Glu Tyr His Arg Asn
        30                  35                  40

ATT CAT CAA CCG CTG GTT GAA ATC TCA CTT TGG GCT TCG CTG GGT            363
Ile His Gln Pro Leu Val Glu Ile Ser Leu Trp Ala Ser Leu Gly
        45                  50                  55

TGG TGG ATT GTC GCG CTA TTG CTG GTG CTG TTT TAC CCA GGT TCC            408
Trp Trp Ile Val Ala Leu Leu Leu Val Leu Phe Tyr Pro Gly Ser
        60                  65                  70

GCA GCA ATC TGG CGT AAC TCT AAA ACA TTG CGC CTT ATT TTT GGC            453
Ala Ala Ile Trp Arg Asn Ser Lys Thr Leu Arg Leu Ile Phe Gly
        75                  80                  85

GTG CTA ACC ATT GTT CCC TTC TTC TGG GGC ATG CTG GCG TTA CGG            498
Val Leu Thr Ile Val Pro Phe Phe Trp Gly Met Leu Ala Leu Arg
        90                  95                  100

GCC TGG CAC TAT GAC GAG AAT CAT TAC AGT GGC GCA ATA TGG CTG            543
Ala Trp His Tyr Asp Glu Asn His Tyr Ser Gly Ala Ile Trp Leu
        105                 110                 115

CTC TAT GTC ATG ATC CTG GTA TGG GGC GCT GAC TCC GGC GCA TAT            588
Leu Tyr Val Met Ile Leu Val Trp Gly Ala Asp Ser Gly Ala Tyr
        120                 125                 130

ATG TTT GGC AAA TTG TTT GGT AAA CAT AAG CTG GCA CCG AAG GTT            633
Met Phe Gly Lys Leu Phe Gly Lys His Lys Leu Ala Pro Lys Val
        135                 140                 145

TCT CCG GGT AAA ACC TGG CAA GGC TTT ATC GGT GGA CTC GCT ACT            678
Ser Pro Gly Lys Thr Trp Gln Gly Phe Ile Gly Gly Leu Ala Thr
        150                 155                 160

GCA GCG GTA ATC TCA TGG GGT TAT GGC ATG TGG GCG AAT CTC GAC            723
Ala Ala Val Ile Ser Trp Gly Tyr Gly Met Trp Ala Asn Leu Asp
        165                 170                 175

GTC GCT CCC GTC ACC TTA CTC ATT TGC TCT ATT GTC GCA GCG TTA            768
Val Ala Pro Val Thr Leu Leu Ile Cys Ser Ile Val Ala Ala Leu
        180                 185                 190

GCC TCA GTG CTC GGC GAT CTG ACC GAG AGT ATG TTT AAG CGT GAA            813
Ala Ser Val Leu Gly Asp Leu Thr Glu Ser Met Phe Lys Arg Glu
        195                 200                 205

GCA GGA ATT AAG GAC AGC GGT CAT TTA ATT CCA GGA CAC GGT GGT            858
Ala Gly Ile Lys Asp Ser Gly His Leu Ile Pro Gly His Gly Gly
        210                 215                 220

ATT TTA GAT CGT ATT GAT AGC CTG ACG GCT GCG GTA CCG GTC TTT            903
Ile Leu Asp Arg Ile Asp Ser Leu Thr Ala Ala Val Pro Val Phe
        225                 230                 235

GCT TGC TTG TTG TTA CTG GTA TTC AGG ACG CTT TAA CGGAAGGTAAT           950
Ala Cys Leu Leu Leu Leu Val Phe Arg Thr Leu ***
        240                 245

ATGCTGAGTT TTCTCTGGGA TTTGGCTTCG TTCATCGTTG CACTGGGTGT ACTTATCACC     1010

GTGCATGAAT TTGGTCATTT CTGGGTTGCC CGGCGTTGTG GTGTTCGCGT TGAGCGTTTC     1070

TCAATAGGGT TTGGTAAGGC GCTCTGGCGG CGAACTGATA AGCTCGGCAC CGAATATGTT     1130

ATCGCCCTGA TCCCGTTGGG CGGTTATGTC AAAATGCTGG ATGAGCGCGC AGAACCGGTC     1190
```

```
GTTCCGGAAC TCCGCCACCA TGCCTTCAAT AATAAATCTG TCGGCCAACG AGCGGCGATT    1250

ATTGCCGCA                                                           1259
```

(2) INFORMATION FOR SEQ ID NO:13:

(i) SEQUENCE CHARACTERISTICS:
        (A) LENGTH: 2289
        (B) TYPE: nucleic acid
        (C) STRANDEDNESS: double stranded
        (D) TOPOLOGY: linear (ii) MOLECULE TYPE: cDNA (iii) HYPOTHETICAL: no (iv) ANTI-SENSE: no (v) FRAGMENT TYPE:

(vi) ORIGINAL SOURCE:
        (A) ORGANISM: yeast
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(ix) FEATURE:
        (A) NAME/KEY: CDP-diacylglycerol synthase (CDS)
        (B) LOCATION:
        (C) IDENTIFICATION METHOD:
        (D) OTHER INFORMATION:

(xi) SEQUENCE DESCRIPTION: SEQ ID NO:13:

```
CTCACTCTTT CAAATTTATT TTTTAATTGC TATTATATAT GGCAACAAAT CTTTCTTATT     60

GTATCTGCCA CCTCATCTCA GCTGCCTTCA TCGAGTATAC TTCATTTGAT TTTCTGATAT    120

TTATTGCTCG TTTTTCGCTA TTTTGATGCA GTACATCTCA GAATTCAACG AGAACGTGG     180

ATATATTAGG CACAAAGAAT CATAAACAAA CGCCCATGTA AATAACTATC AATACACTAC    240

TTTCTAAACC AATCTGCAGG AGCTCCACCT TGATCGCTTT GGCTTATTCC AGGCGTTTTC    300

AGGCACTGTA TATTGGTACT ATATCGCTAT GTATTTGACA GTCATTATCA ACGGATACCC    360

TTCTTGAAAA TTTTTCAGAT GGGATGACAT GTGAAAAGTG TAACAATCGA GAACTGTAAA    420

CAGCATGGGG GAGCATTCAT CAATATTGTT ATTTAGTGTA AGCCAGATTG TGAAGACGCA    480

CTTCTTGCCA AGTATCTTCC CAAACAGCGA ACCTGTCATA CTTAACTGTT CCACTTCCAT    540

ATACCTAAA ATG TCT GAC AAC CCT GAG ATG AAA CCA CAT GGT ACG AGC        588
           Met Ser Asp Asn Pro Glu Met Lys Pro His Gly Thr Ser
                             5                  10

AAG GAG ATT GTG GAG TCG GTT ACT GAC GCC ACC TCA AAG GCG ATT          633
Lys Glu Ile Val Glu Ser Val Thr Asp Ala Thr Ser Lys Ala Ile
 15                  20                  25

GAT AAA TTG CAA GAA GAA CTC CAC AAG GAC GCC AGC GAA TCC GTC          678
Asp Lys Leu Gln Glu Glu Leu His Lys Asp Ala Ser Glu Ser Val
         30                  35                  40

ACG CCG GTG ACC AAG GAA AGC ACT GCT GCT ACA AAG GAA AGC AGG          723
Thr Pro Val Thr Lys Glu Ser Thr Ala Ala Thr Lys Glu Ser Arg
     45                  50                  55

AAA TAC AAC TTT TTC ATT AGA ACA GTT TGG ACG TTT GTT ATG ATC          768
Lys Tyr Asn Phe Phe Ile Arg Thr Val Trp Thr Phe Val Met Ile
 60                  65                  70
```

```
AGT GGT TTC TTC ATC ACC TTA GCA TCG GGT CAT GCA TGG TGT ATA      813
Ser Gly Phe Phe Ile Thr Leu Ala Ser Gly His Ala Trp Cys Ile
 75              80                  85

GTG CTG ATT TTG GGC TGC CAA ATT GCT ACT TTT AAA GAG TGT ATT      858
Val Leu Ile Leu Gly Cys Gln Ile Ala Thr Phe Lys Glu Cys Ile
 90              95                 100

GCC GTA ACA AGT GCA TCT GGT CGC GAA AAG AAT TTG CCA TTG ACA      903
Ala Val Thr Ser Ala Ser Gly Arg Glu Lys Asn Leu Pro Leu Thr
    105             110                 115

AAG ACG TTG AAC TGG TAC CTT CTC TTC ACC ACT ATC TAT TAC TTA      948
Lys Thr Leu Asn Trp Tyr Leu Leu Phe Thr Thr Ile Tyr Tyr Leu
    120             125                 130

GAT GGG AAA TCA CTC TTC AAG TTT TTC CAA GCT ACT TTT TAC GAG      993
Asp Gly Lys Ser Leu Phe Lys Phe Phe Gln Ala Thr Phe Tyr Glu
    135             140                 145

TAT CCT GTA TTG AAC TTT ATC GTA ACA AAT CAT AAG TTT ATC TGC     1038
Tyr Pro Val Leu Asn Phe Ile Val Thr Asn His Lys Phe Ile Cys
    150             155                 160

TAT TGT CTC TAT CTT ATG GGA TTT GTT CTG TTC GTT TGT AGT TTA     1083
Tyr Cys Leu Tyr Leu Met Gly Phe Val Leu Phe Val Cys Ser Leu
165             170                 175

AGA AAG GGA TTT TTG AAA TTC CAG TTC GGA TCA TTG TGC GTT ACT     1128
Arg Lys Gly Phe Leu Lys Phe Gln Phe Gly Ser Leu Cys Val Thr
180             185                 190

CAT ATG GTT CTT CTT CTG GTA GTA TTT CAG GCT CAT TTG ATC ATC     1173
His Met Val Leu Leu Leu Val Val Phe Gln Ala His Leu Ile Ile
    195             200                 205

AAA AAC GTG CTC AAT GGG CTA TTC TGG TTC TTA TTA CCA TGC GGG     1218
Lys Asn Val Leu Asn Gly Leu Phe Trp Phe Leu Leu Pro Cys Gly
    210             215                 220

TTG GTA ATT GTT AAT GAT ATC TTC GCC TAC CTG TGC GGC ATT ACA     1263
Leu Val Ile Val Asn Asp Ile Phe Ala Tyr Leu Cys Gly Ile Thr
    225             230                 235

TTC GGT AAG ACT AAA CTA ATA GAA ATC TCG CCC AAG AAA ACT TTA     1308
Phe Gly Lys Thr Lys Leu Ile Glu Ile Ser Pro Lys Lys Thr Leu
    240             245                 250

GAA GGT TTC CTT GGT GCC TGG TTT TTC ACT GCT CTA GCT AGT ATT     1353
Glu Gly Phe Leu Gly Ala Trp Phe Phe Thr Ala Leu Ala Ser Ile
    255             260                 265

ATA TTA ACA AGG ATT CTG AGC CCT TAT ACT TAC TTG ACG TGC CCT     1398
Ile Leu Thr Arg Ile Leu Ser Pro Tyr Thr Tyr Leu Thr Cys Pro
    270             275                 280

GTT GAA GAT CTC CAT ACC AAT TTT TTC TCT AAT TTG ACA TGT GAA     1443
Val Glu Asp Leu His Thr Asn Phe Phe Ser Asn Leu Thr Cys Glu
    285             290                 295

CTA AAC CCA GTT TTC CTT CCA CAA GTT TAC AGA CTT CCA CCC ATC     1488
Leu Asn Pro Val Phe Leu Pro Gln Val Tyr Arg Leu Pro Pro Ile
    300             305                 310

TTT TTC GAT AAA GTT CAA ATC AAT TCA ATT ACA GTA AAA CCA ATT     1533
Phe Phe Asp Lys Val Gln Ile Asn Ser Ile Thr Val Lys Pro Ile
    315             320                 325

TAT TTC CAT GCT TTA AAC TTA GCT ACC TTT GCA TCA TTA TTT GCG     1578
Tyr Phe His Ala Leu Asn Leu Ala Thr Phe Ala Ser Leu Phe Ala
    330             335                 340

CCA TTT GGA GGC TTT TTC GCA TCT GGT CTA AAG AGA ACT TTT AAA     1623
Pro Phe Gly Gly Phe Phe Ala Ser Gly Leu Lys Arg Thr Phe Lys
    345             350                 355

GTT AAA GAC TTT GGC CAC TCC ATC CCA GGC CAT GGT GGT ATC ACA     1668
Val Lys Asp Phe Gly His Ser Ile Pro Gly His Gly Gly Ile Thr
    360             365                 370
```

```
GAC AGG GTT GAT TGC CAA TTC ATA ATG GGT TCT TTT GCC AAT TTG         1713
Asp Arg Val Asp Cys Gln Phe Ile Met Gly Ser Phe Ala Asn Leu
    375                 380                 385

TAC TAT GAA ACA TTC ATC AGC GAA CAC AGA ATA ACA GTA GAT ACA         1758
Tyr Tyr Glu Thr Phe Ile Ser Glu His Arg Ile Thr Val Asp Thr
    390                 395                 400

GTT TTA TCC ACT ATT TTA ATG AAC CTG AAC GAC AAG CAG ATT ATA         1803
Val Leu Ser Thr Ile Leu Met Asn Leu Asn Asp Lys Gln Ile Ile
    405                 410                 415

GAA TTG ATT GAT ATC TTG ATT AGA TTC CTA TCT AAA AAA GGT ATA         1848
Glu Leu Ile Asp Ile Leu Ile Arg Phe Leu Ser Lys Lys Gly Ile
    420                 425                 430

ATA TCA GCG AAG AAT TTT GAA AAG TTG GCT GAC ATC TTT AAT GTG         1893
Ile Ser Ala Lys Asn Phe Glu Lys Leu Ala Asp Ile Phe Asn Val
    435                 440                 445

ACC AAG AAA TCA TTG ACC AAT CAC TCT TGA ATATAAAAAGACCATATA          1942
Thr Lys Lys Ser Leu Thr Asn His Ser ***
    450                 455

AAAGTATATA TGAGTGTATG AATAGTTTTT TTTTTTCAAA CTTATGCACG CTATACTACT   2002

CTTTCCCTAT TTAGTTTATG TAAATTATAA AATATGATAT CAATTCTTTA ACAAAATTTC   2062

TCGCTCGTTT TTATACTTAT GACTATATGT AGGAAAATAA ACGTGTTGCT CTGTCATGTT   2122

ACTTCTAAAA TATTGAGAGG AGAAAAAAAA AAAAAAAAA AAAATTATAA ACAAATGAAA    2182

AAAGGACGTA CTGACTAATA GTAAGTAGAT CTTTTACCTG GAAGGTGCCC TATGATAAGA   2242

TTTTTCATCA ACCAATCTAG CTGAGCATAC TGTTGGCAGT AATTAGG                 2289
```